(12) United States Patent
Uchimura et al.

(10) Patent No.: US 7,963,914 B2
(45) Date of Patent: Jun. 21, 2011

(54) ENDOSCOPE

(75) Inventors: Sumihiro Uchimura, Sagamihara (JP);
Akira Taniguchi, Hachioji (JP);
Fumiyuki Onoda, Tama (JP); Toshiaki Noguchi, Tachikawa (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1279 days.

(21) Appl. No.: 11/584,484

(22) Filed: Oct. 20, 2006

(65) Prior Publication Data
US 2007/0038023 A1 Feb. 15, 2007

Related U.S. Application Data

(63) Continuation of application No. PCT/JP2005/007795, filed on Apr. 25, 2005.

(30) Foreign Application Priority Data

Apr. 26, 2004 (JP) .................................. 2004-130124

(51) Int. Cl.
*A61B 1/04* (2006.01)
*A61B 1/12* (2006.01)
(52) U.S. Cl. ........................................ 600/156; 600/109
(58) Field of Classification Search .......... 600/109–110, 600/132–133, 153, 156, 158–159
See application file for complete search history.

(56) References Cited

U.S. PATENT DOCUMENTS

| | | | | |
|---|---|---|---|---|
| 4,901,142 A | * | 2/1990 | Ikuno et al. | 348/69 |
| 5,447,148 A | * | 9/1995 | Oneda et al. | 600/131 |
| 5,840,024 A | | 11/1998 | Taniguchi et al. | |
| 5,879,288 A | * | 3/1999 | Suzuki et al. | 600/176 |
| 5,888,191 A | * | 3/1999 | Akiba et al. | 600/153 |
| 6,059,718 A | * | 5/2000 | Taniguchi et al. | 600/117 |
| 6,099,465 A | * | 8/2000 | Inoue | 600/134 |
| 6,840,901 B2 | | 1/2005 | Onishi et al. | |
| 2001/0051766 A1 | * | 12/2001 | Gazdzinski | 600/309 |
| 2001/0055061 A1 | * | 12/2001 | Onishi et al. | 348/65 |
| 2002/0198439 A1 | * | 12/2002 | Mizuno | 600/109 |
| 2003/0069475 A1 | | 4/2003 | Banik et al. | |
| 2004/0073086 A1 | * | 4/2004 | Abe | 600/109 |
| 2004/0082834 A1 | | 4/2004 | Onishi et al. | |

FOREIGN PATENT DOCUMENTS

| | | |
|---|---|---|
| JP | 05-307143 | 11/1993 |
| JP | 08-000542 | 1/1996 |
| JP | 10-295635 | 11/1998 |
| JP | 11-056774 | 3/1999 |
| JP | 2000-310739 | 11/2000 |

(Continued)

OTHER PUBLICATIONS

Chinese Office Action dated Mar. 10, 2010.

*Primary Examiner* — Philip R Smith
(74) *Attorney, Agent, or Firm* — Scully, Scott, Murphy & Presser, PC

(57) ABSTRACT

In an endoscope, air/water feed pipe lines are arranged through an elongated insertion portion having an image pickup unit at its front end. In an operation portion arranged at the rear end of the insertion portion, there are provided an antenna, and a wireless transmission unit for wirelessly transmitting, using this antenna, information including image data on a subject picked up by the image pickup unit, to endoscope peripheral apparatuses in the outside.

15 Claims, 23 Drawing Sheets

FOREIGN PATENT DOCUMENTS

| | | |
|---|---|---|
| JP | 2001-125012 | 5/2001 |
| JP | 2001-275950 | 10/2001 |
| JP | 2001-353124 | 12/2001 |
| JP | 2002-238074 | 8/2002 |
| JP | 2002-282199 | 10/2002 |
| JP | 2003-275164 | 9/2003 |
| JP | 2004-80597 | 3/2004 |

* cited by examiner

WIRELESS TYPE

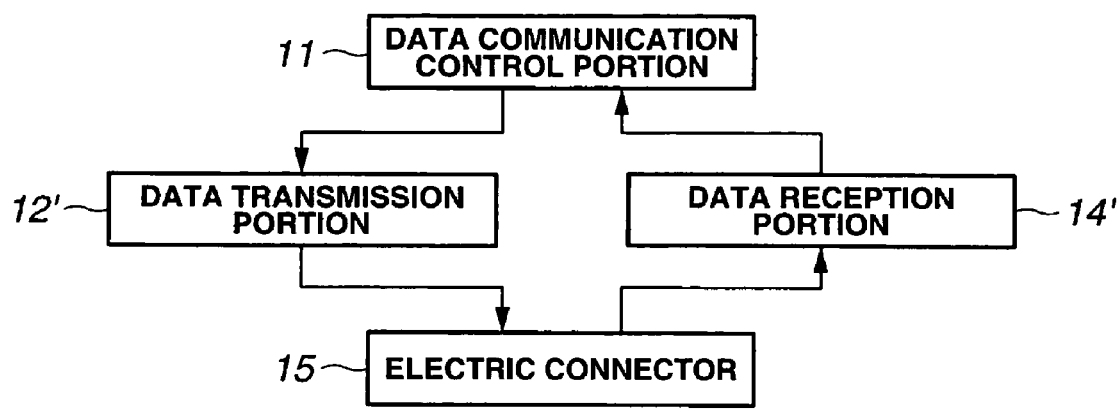
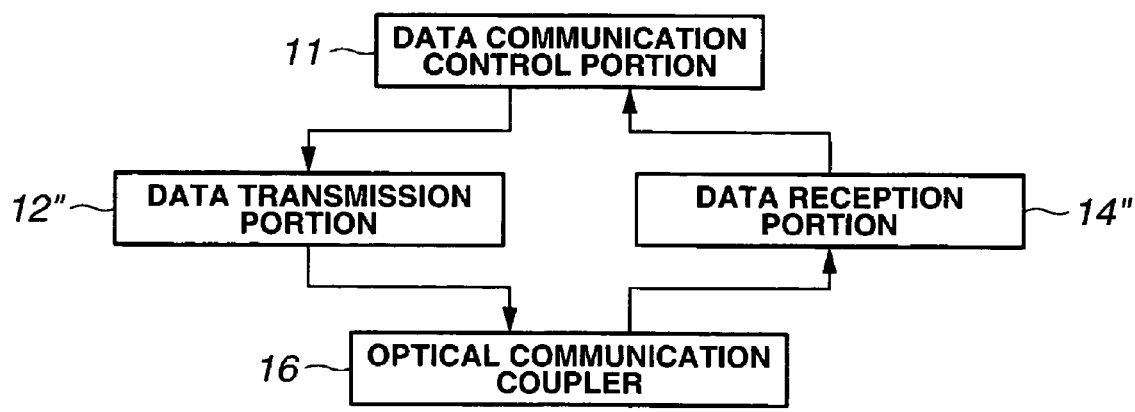

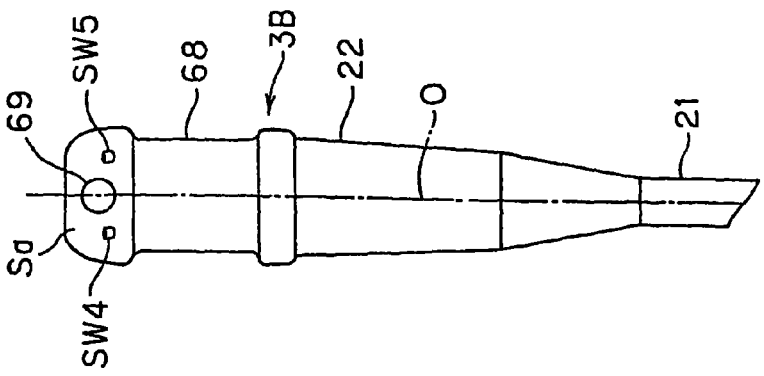
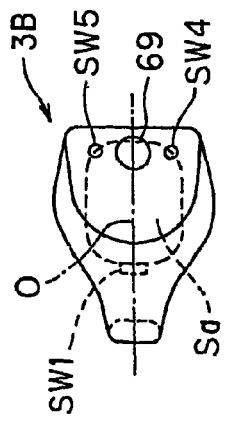
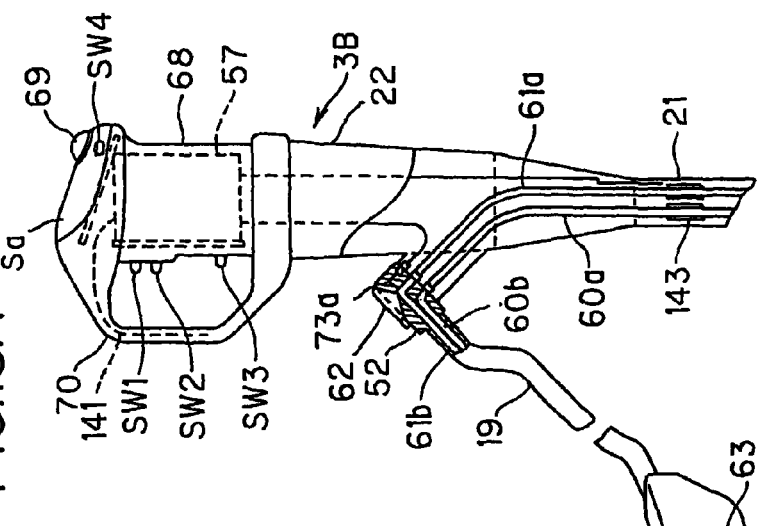
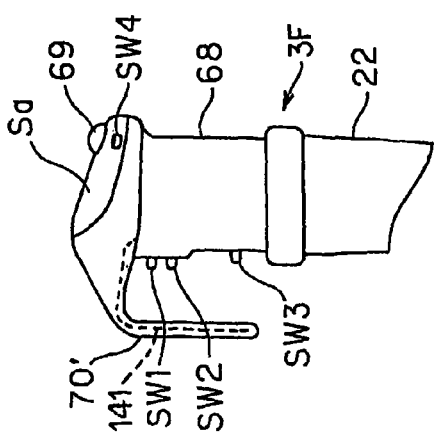

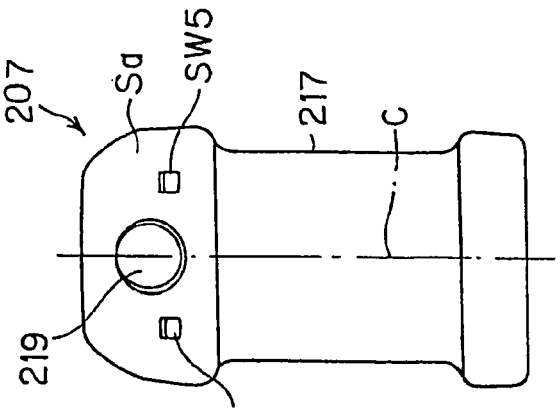
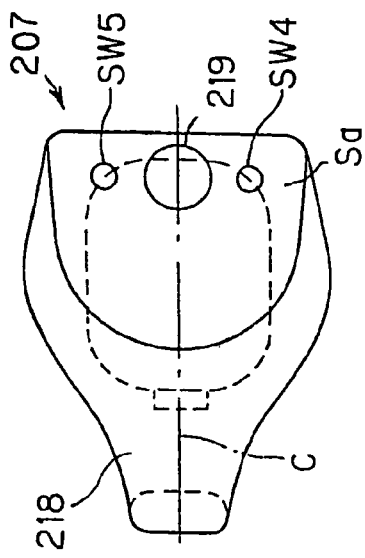
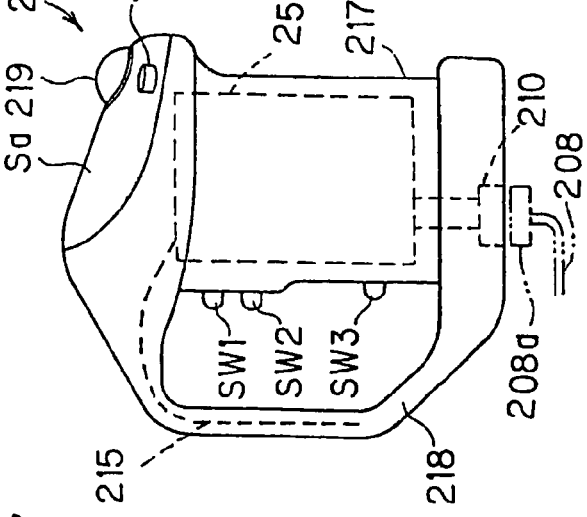
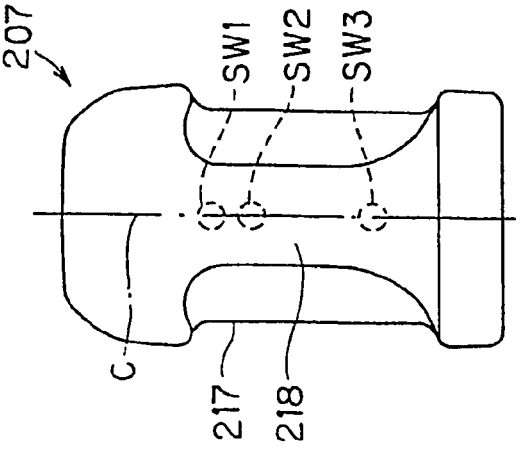

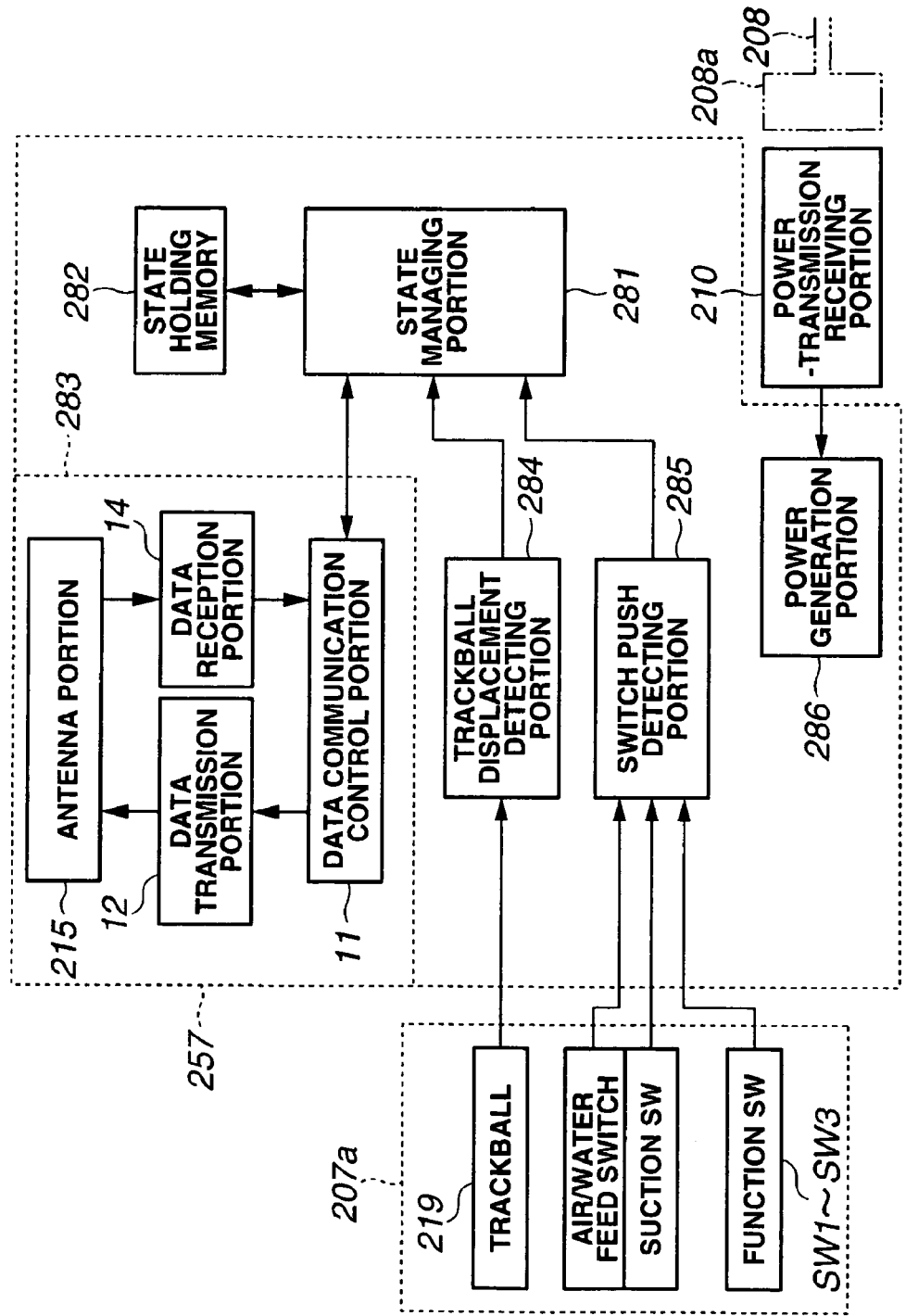

US 7,963,914 B2

ENDOSCOPE

CROSS REFERENCES TO RELATED APPLICATIONS

This application is a continuation application of PCT/JP2005/007795 filed on Apr. 25, 2005 and claims benefit of Japanese Application No. 2004-130124 filed in Japan on Apr. 26, 2004, the entire contents of which are incorporated herein by this reference.

BACKGROUND OF THE INVENTION

1. Field of the Invention

The present invention relates to an endoscope that is inserted into a body cavity or the like to perform an endoscope examination or the like.

2. Description of the Related Art

The endoscope having an image pickup element in its insertion portion has been widely used in examinations inside the body cavity and treatments using treatment tools.

In the endoscope incorporating the image pickup element like this, a universal cable through which a light guide for transmitting illumination light and a signal line connected to the image pickup element are arranged, are extended from an operation portion provided on the rear end side of the insertion portion.

Through the universal cable, pipe lines for performing air/water feed and suction are arranged.

On the other hand, as a conventional example, Japanese Unexamined Patent Application Publication No. 2001-353124 discloses an endoscope wherein illumination means is formed without using a light guide, and image pickup signals obtained by image pickup means are transmitted by radio, thereby eliminating the need for a universal cable.

SUMMARY OF THE INVENTION

In the present invention, there is provided an endoscope that includes an elongated insertion portion having therein an air/water feed pipe line; an operation portion provided at the rear end of the insertion portion; an image pickup portion for picking up an image of a subject, the image pickup portion being provided at the front end part of the insertion portion; an antenna provided in the operation portion; and a wireless transmission portion for wirelessly transmitting, using the antenna, information including image data on the subject obtained by the image pickup portion, to endoscope peripheral apparatuses in the outside.

BRIEF DESCRIPTION OF THE DRAWINGS

FIGS. 2A to 2C are diagrams showing data transmission configurations used in the present invention, wherein FIGS. 2A, 2B, and 2C, respectively, show data transmission configurations of wireless type, wired type, and optical communication type;

FIGS. 18A to 18D are diagrams each showing an endoscope according to a second embodiment of the present invention;

FIGS. 20A to 20D are diagrams each showing an remote operation controller; and

FIG. 21 is a block diagram showing the configuration of an electronic system of the remote operation controller.

DESCRIPTION OF THE PREFERRED EMBODIMENTS

Hereinafter, embodiments according to the present invention will be described with reference to the accompanying drawings.

First Embodiment

An endoscope according to a first embodiment of the present invention is explained with reference to FIGS. 1 to 17.

Prior to description of the specific configuration of the present invention, a general outline of the endoscope according to the present invention will be given with reference to FIGS. 1 to 3.

Figure 1:
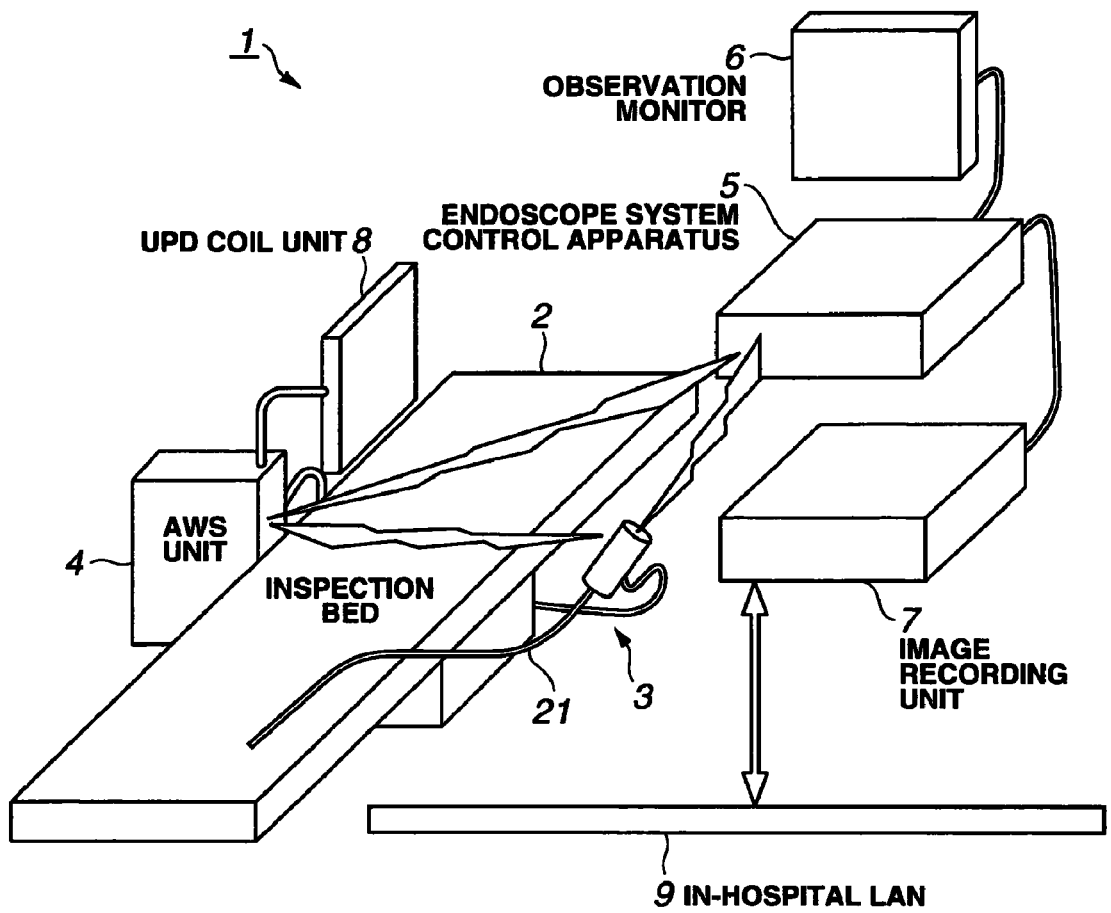
FIG. 1 is a diagram showing the schematic configuration of an endoscope system having an endoscope according to the present invention.

As shown in FIG. 1, an endoscope system 1 according to the present invention includes a flexible endoscope (also referred to as a scope) 3 that is inserted into the body cavity of a patient (not shown) lying on an inspection bed, to make an endoscope examination; an air/water feed and suction unit (hereinafter abbreviated as an AWS unit) 4 that is connected to the endoscope 3 and that has functions of air/water feed and suction; an endoscope system control apparatus 5 for performing signal processing with respect to an image pickup element incorporated in the endoscope 3 and control processing with respect to various operating means provided in the endoscope 3; and an observation monitor 6 by a liquid crystal monitor or the like that displays video signals generated by the endoscope system control apparatus 5.

The endoscope system 1 further includes an image recording unit 7 for filing e.g., digital video signals generated by the endoscope system control apparatus 5; and a UPD coil unit 8 (UPD is an abbreviation of Endoscope Position Detecting Coil Unit) for displaying the shape of the insertion portion of the endoscope 3 by detecting the position of each UPD coil, e.g., through the reception of a signal from an electromagnetic field generated by each UPD coil, provided that the UPD coil unit 8 is connected to the AWS unit 4 and the shape detecting coil, or UPD coils are incorporated in the insertion portion of the endoscope 3.

The image recording unit 7 is connected to a LAN 9 in a hospital having the endoscope system 1, and is adapted to be able to make reference to images or the like filed in the image recording unit 7 by each terminal apparatus that is wiredly or wirelessly connected to the LAN 9.

As shown in FIG. 1, the AWS unit 4 and endoscope system control apparatus 5 are adapted to perform transmission/reception of information (data) therebetween by radio. Also, the endoscope 3 performs transmission/reception of information (data) to/from the AWS unit 4 and endoscope system control apparatus 5 (i.e., interactive information transmission therebetween) by radio.

Figure 2A:
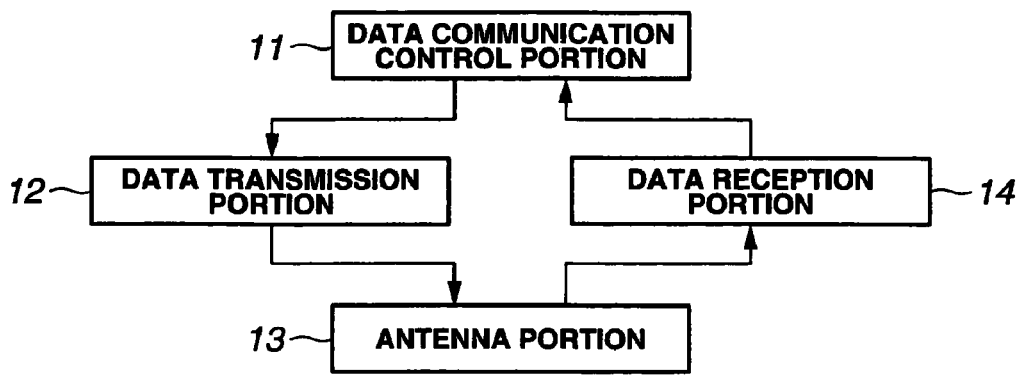
Figure 3:
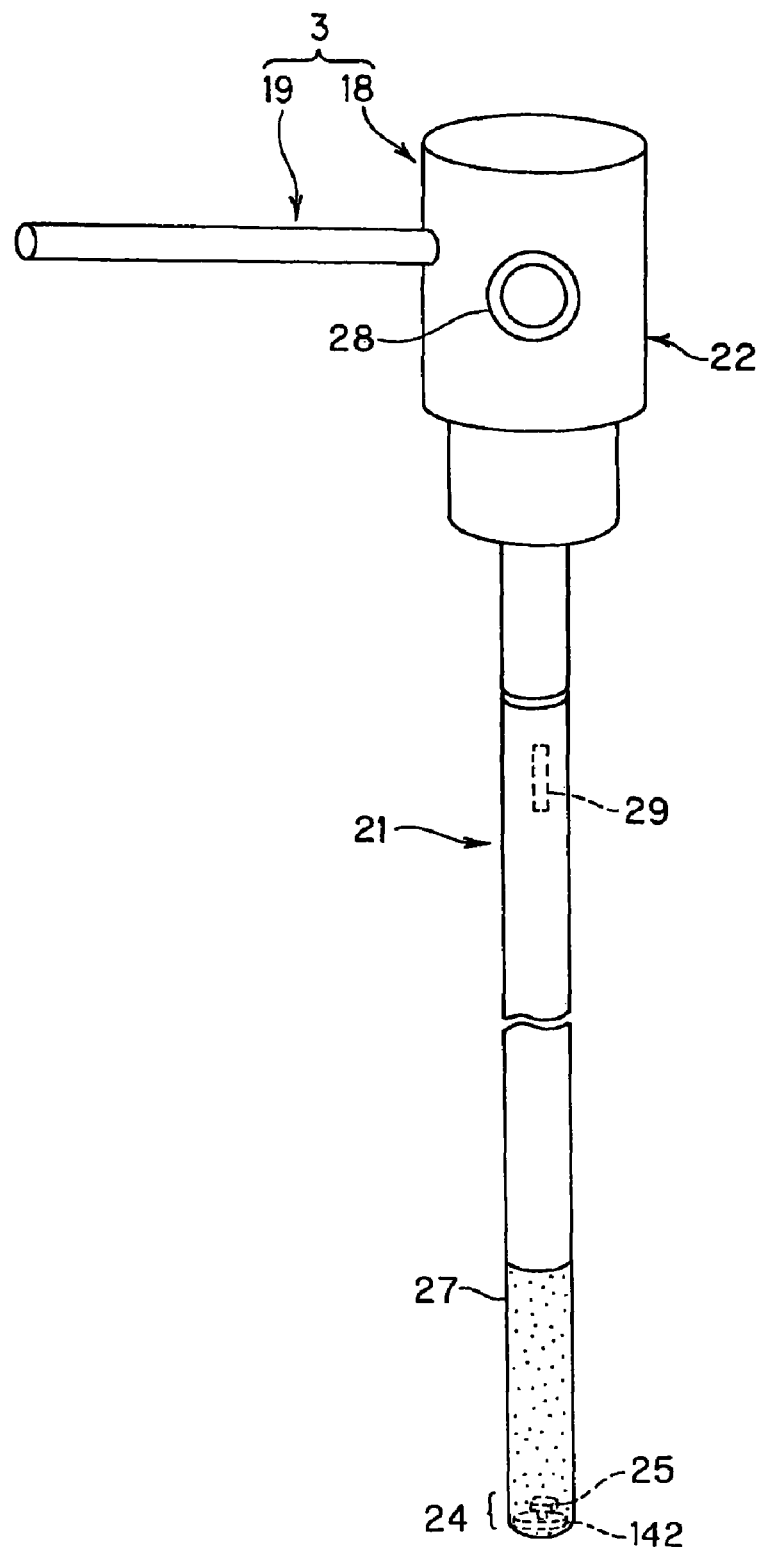
FIG. 3 is a diagram showing the schematic configuration of the endoscope according to the present invention.

FIGS. 2A to 2C shows three methods in transmission/reception units (communications portions) that perform data transmission/reception between a unit and apparatus, or between the endoscope 3 and a unit or apparatus.

FIG. 2A shows a wireless type data transmission/reception unit (information transmission means). Here, description is made of the case where a data transmission/reception is performed between the AWS unit 4 and endoscope system control apparatus 5.

By a data communication control portion 11 incorporated in the AWS unit 4, data for transmission is modulated through a data transmission portion 12, and transmitted from an antenna portion 13 to the endoscope system control apparatus 5 by radio.

Also, the AWS unit 4 receives, by the antenna portion 13, data transmitted from the endoscope system control apparatus 5 by radio, and after having demodulated it by a data reception portion 14, sends the data to the data communication control portion 11. In this embodiment, when data is transmitted by radio, a wireless LAN of which the maximum data communication speed is 54 Mbps is constructed based on, for example, IEEE802.11g standard.

FIG. 2B shows a wired type data transmission/reception unit. Here, as a specific example, description is made of the case where a data transmission/reception is performed between the endoscope 3 and AWS unit 4. By a data communication control portion 11 incorporated in the endoscope 3, data transmitted from the endoscope 3 passes through a data transmission portion 12', and is transmitted from an electrical connector 15 to the AWS unit 4 by wire. Also, data transmitted from the AWS unit 4 is sent to the data communication control portion 11 through the electrical connector 15 and a data reception portion 14'.

FIG. 2C shows an optical communication type data transmission/reception unit. Here, as a specific example, description is made of the case where a data transmission/reception is performed between the AWS unit 4 and endoscope system control apparatus 5. The data communication control portion 11 incorporated in the AWS unit 4 is connected to an optical communication coupler 16 provided in this AWS unit 4 via a data transmission portion 12" and data reception portion 14" that perform transmission and reception by light, and performs data transmission/reception via the optical communication coupler on the side of the endoscope system control apparatus 5. FIG. 3 shows a schematic configuration of the endoscope 3 according to the present invention. The endoscope 3 includes an endoscope body 18, and a tube unit 19 detachably connected to the endoscope body 18 and being of a throwaway type (disposable pipe).

The tube unit 19 is made thinner than the conventional universal cable, and in this embodiment, it is constituted of only two air/water feed pipe lines 60b and 61b, and a power supply line 73a, as will be described later.

The endoscope body 18 includes a flexible insertion portion 21 to be inserted into the body cavity and an operation portion 22 provided at the rear end of the insertion portion 21, and the base end of the tube unit 19 is detachably connected to the operation portion 22.

At a front end portion 24 of the insertion portion 21, as an image pickup element, there is provided an image pickup unit using a CCD 25 that can variably adjust the gain inside the image pickup element. Also, at the front end portion 24, there may be provided a contact sensor 142 for detecting a state in which the front end portion 24 has made contact (pressure contact) with inner walls or the like in the body cavity.

Furthermore, at the rear end of the front end portion 24, there is provided a bending portion 27 that can be bent by a low amount of force. By operating an angle/remote control operator 28 arranged in the operation portion 22, the bending portion 27 can be bent. The angle/remote control operator 28 is adapted to be able to perform remote control operations such as an angle operation (bending operation), operations such as an air/water feed and suction, and remote control operations with respect to the endoscope system control apparatus 5 and the like (specifically, freeze instruction operation and release instruction operation). Also, in the insertion portion 21, portions of which the hardness can be variably adjusted are formed so as to allow an insertion or the like to be smoothly performed.

Here, a cleaning level detector 29 may be arranged in the insertion portion 21 so as be able to detect the cleaning level or the like of the pipe lines.

Next, more specific configuration of the endoscope system 1 will be described with reference to FIG. 4.

Adjacently to the side surface of the inspection bed 2, the observation monitor 6 comprising a liquid crystal monitor is arranged. Moreover, the endoscope system control apparatus 5, the AWS unit 4, image files/LAN/electric scalpel/ultrasonic unit (which is an abbreviated expression for image file unit, wireless LAN or wired LAN, electric knife unit, ultrasonic unit etc.) 32, are mounted on a cart 31 movably arranged in the vicinity of one of the lengthwise ends of the inspection bed 2, in a stacked manner. On the top of this stack, a monitor 33 with a touch panel is mounted.

Also, on the upper portion of the surface of the inspection bed 2 on which a patient lies, a UPD coil unit 8 is embedded. The UPD coil unit 8 is connected to the AWS unit 4 by a UPD cable 34.

Figure 6:
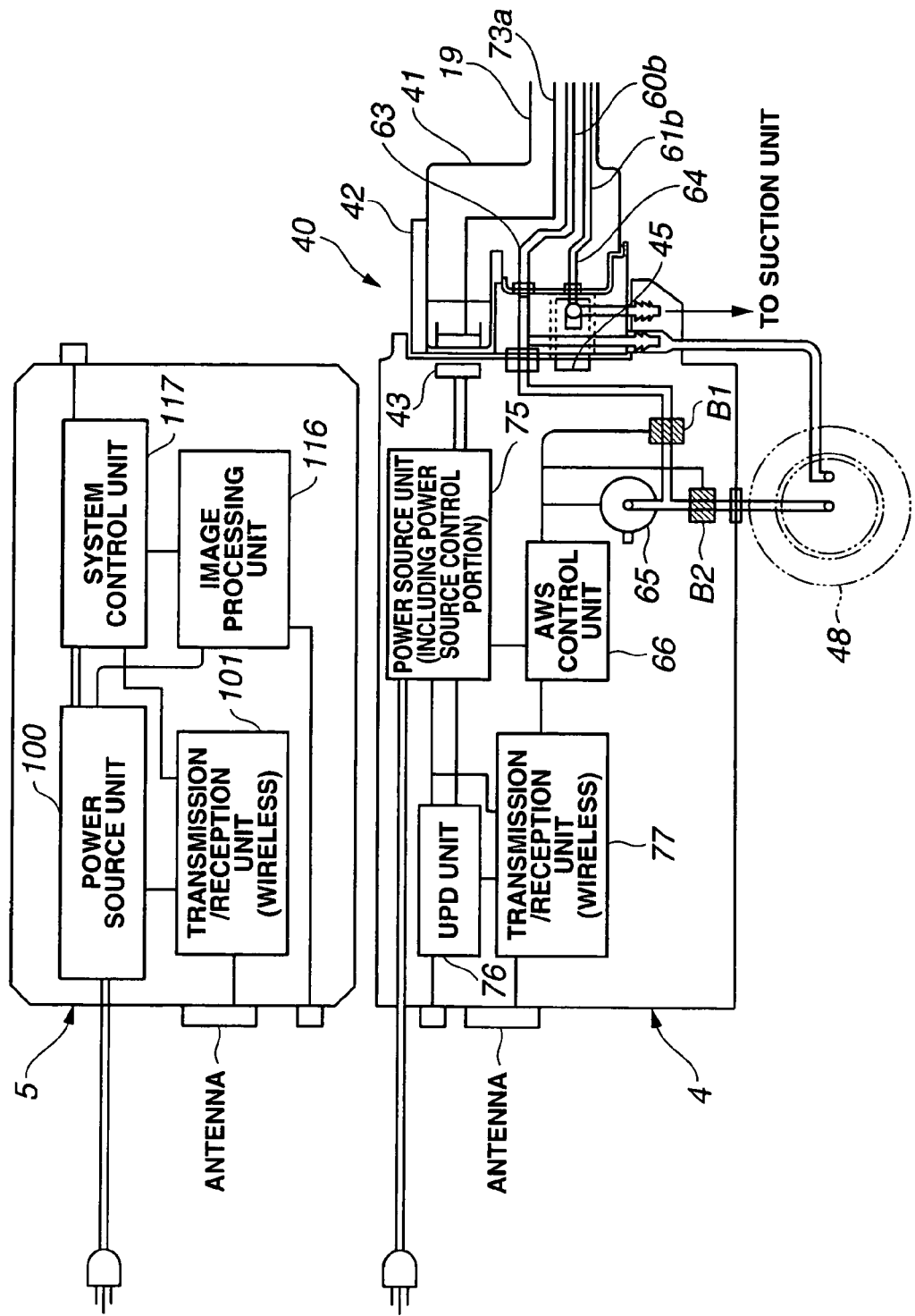
FIG. 6 is a diagram showing the configuration of an AWS adapter.

In this embodiment, as shown in FIG. 6 for example, the AWS unit 4 and endoscope system control apparatus 5 perform data transmission/reception therebetween by wireless transmission/reception units 77 and 101. As shown in FIG. 4, the observation monitor 6 is connected to a monitor connector of the endoscope system control apparatus 5 by a monitor cable 35.

Figure 4:
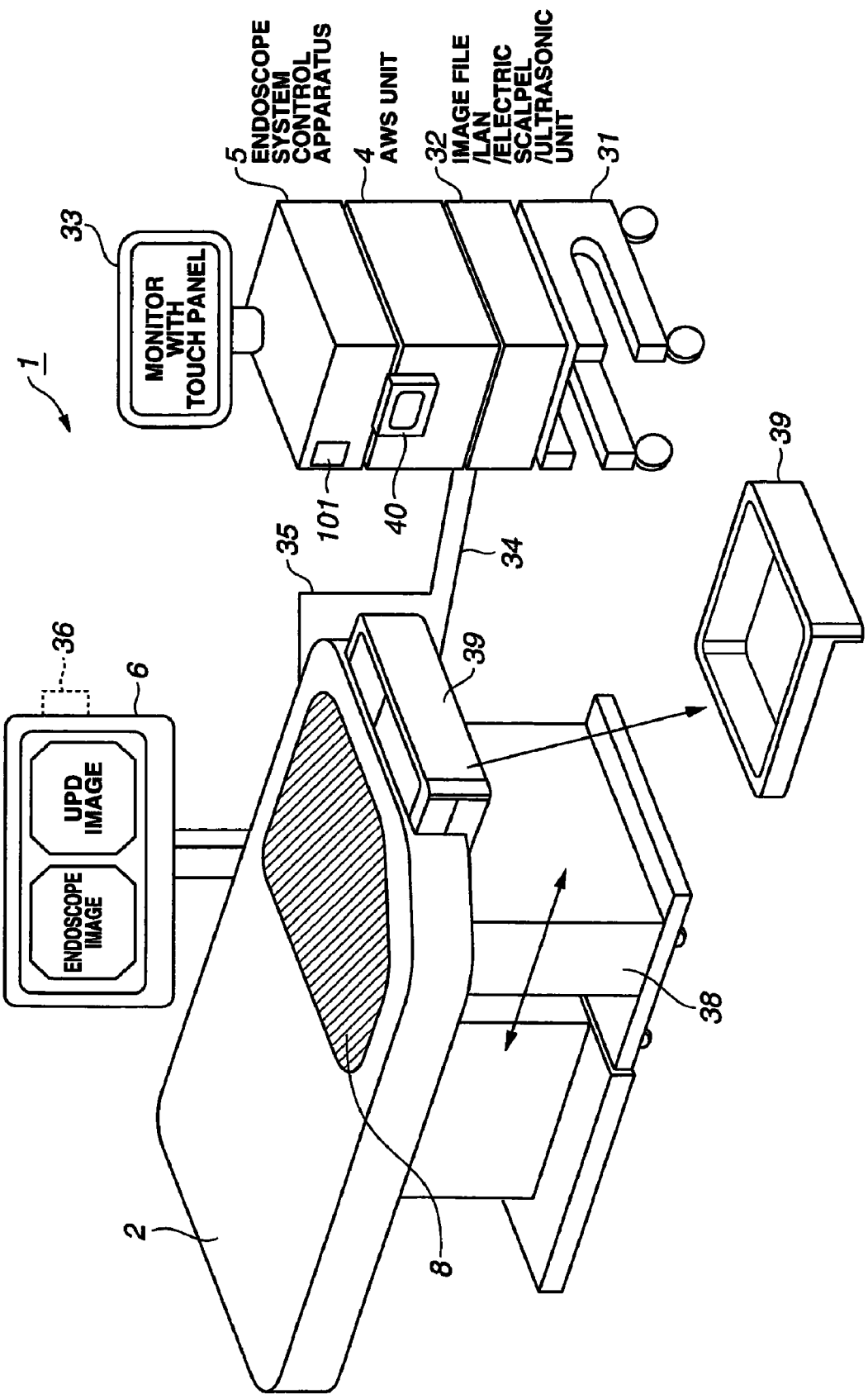
FIG. 4 is a perspective view showing the overall configuration of the endoscope system having an endoscope according to a first embodiment of the present invention.

As shown in FIG. 4, the arrangement may be such that transmission/reception units 101 and 36 are mounted on the endoscope system control apparatus 5 and the observation monitor 6, respectively, and that video signals are transmitted from the endoscope system control apparatus 5 to the observation monitor 6 so that an endoscope image corresponding to the video signals can be displayed on the display surface thereof.

As will be described later, to the endoscope system control apparatus 5, image data picked up by the CCD 25 is transmitted from the endoscope 3, as well as image data on the insertion portion shape (UPD image) of the endoscope 3, detected using the UPD coil unit 8 from the side of the AWS unit 4, is transmitted. Therefore, the endoscope system control apparatus 5 is adapted to send video signals corresponding to the image data to the observation monitor 6 so that the UPD image can be displayed together with the endoscope image on the display surface thereof.

In order to allow a plurality of kinds of images to be simultaneously displayed on its display surface in this manner, the observation monitor 6 is constituted of a monitor of a high-definition television (HDTV).

Figure 7:
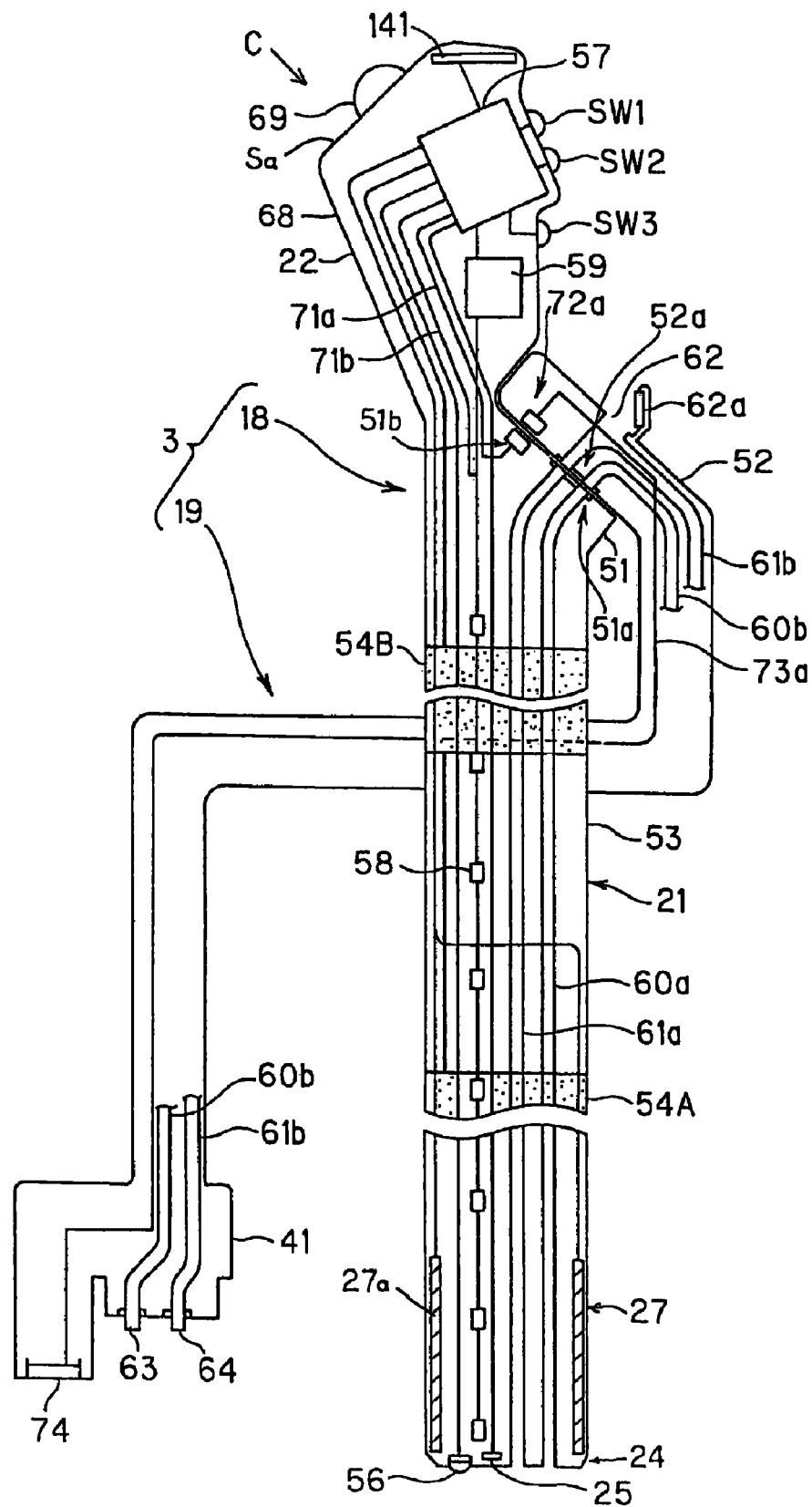
FIG. 7 is an overall view showing a detailed configuration of the endoscope according to the first embodiment of the present invention.

Also, in this embodiment, at one of the lengthwise ends of the inspection bed 2 and at a position therebelow, a concave portion for accommodation is formed so that a tray conveying trolley 38 can be slidably accommodated in this concave portion for accommodation. A scope tray 39 in which the endoscope 3 shown in FIG. 7 is accommodated is mounted on the tray conveying trolley 38.

The scope tray 39 in which the disinfected or sterilized endoscope 3 is accommodated can be conveyed by the tray conveying trolley 38 and can be accommodated in the concave portion of the inspection bed 2. An operator can draw the endoscope 3 from the scope tray 39 and use it for an endoscope examination, and after the endoscope examination has been finished, the operator has only to accommodate the endoscope in the scope tray 39. Thereafter, by conveying the scope tray 39 containing the endoscope 3 after use by the tray conveying trolley 38, the disinfection or sterilization can also be smoothly performed.

As shown in FIG. 4, for example, the AWS unit 4 has a scope connector 40. As shown in FIG. 6, a scope connector 41 for the endoscope 3 is detachably connected to the scope connector 40.

Figure 5:
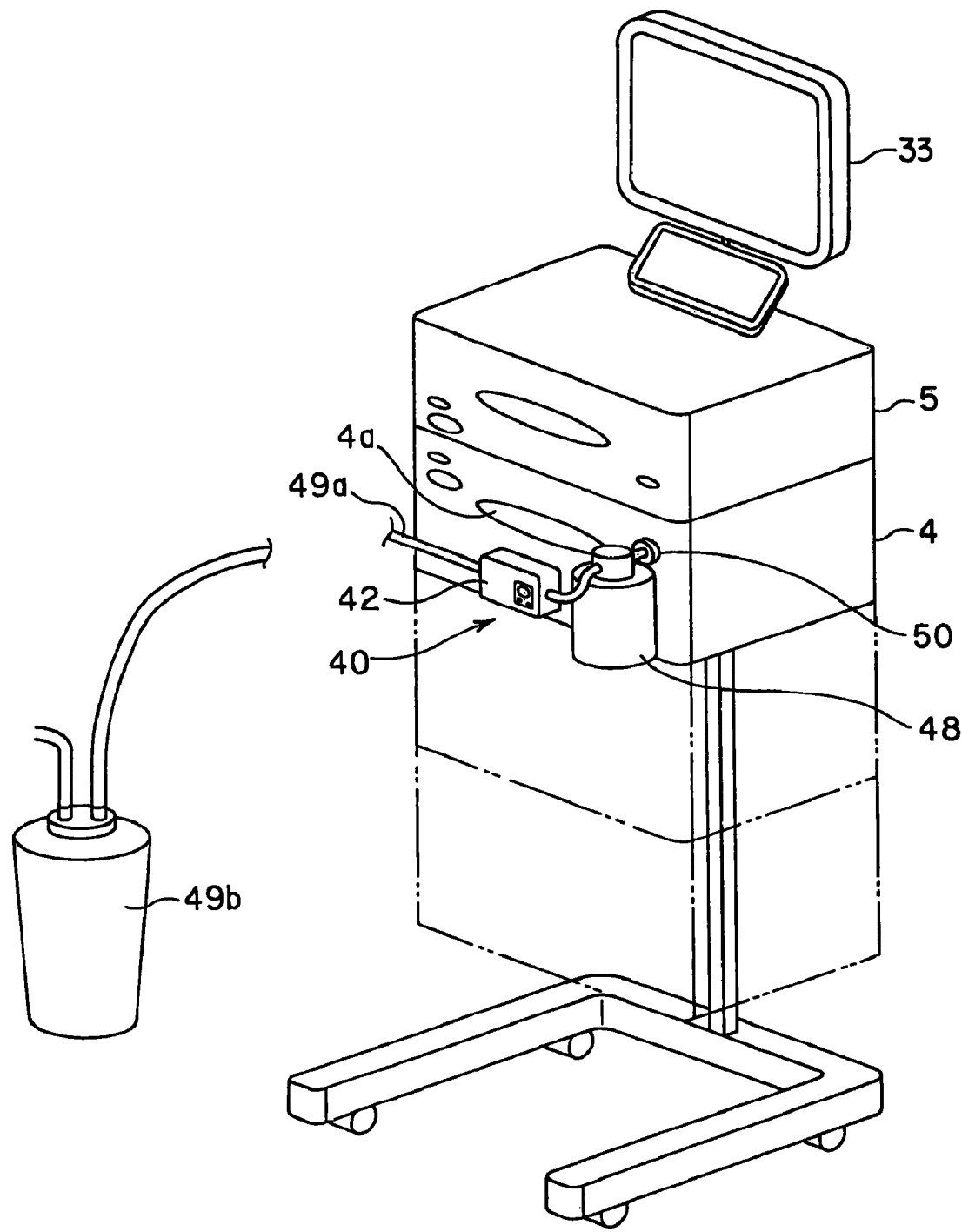
FIG. 5 is a perspective view showing specific external shapes of the peripheries of an AWS unit.

Here, more specific external shape of the scope connector 40 on the side of the AWS unit 4 is shown in FIG. 5. Also, FIG. 6 shows the internal structure of the scope connector 40 on the side of the AWS unit 4, and the scope connector 41 on the side of the endoscope 3, in association with their connection states.

In actuality, as shown in FIG. 6, a recess-shaped AWS adapter mounting portion is mounted on the front of the AWS unit 4. By mounting an AWS adapter (pipe line connection adapter) 42 on this AWS adapter mounting portion, the scope connector 40 is formed, and the scope connector 41 of the endoscope 3 is connected to this scope connector 40.

On the AWS adapter mounting portion, there are provided an electricity connector 43 for scope connection, an air feed connector, and a pinch valve 45. The inner end face of the AWS adapter 42 is detachably mounted on the AWS adapter mounting portion, and the scope connector 41 of the endoscope 3 is connected to the AWS adapter mounting portion from the side of the outer end face of the AWS adapter 42.

Next, specific configuration of the endoscope 3 according to the first embodiment of the present invention will be described with reference to FIG. 7.

As its outline has been described above with reference to FIG. 3, the endoscope 3 according to this embodiment includes the endoscope body 18 having the flexible insertion portion 21 and operation portion 22 provided at the rear end thereof; and the tube unit 19 having an overall connector portion 52 located at the base end thereof. The tube unit 19 is a throwaway type. The overall connector portion 52 is detachably connected to a connector portion 51 (for tube unit connection) provided in the vicinity of the base end (front end) of the operation portion 22 in the endoscope body 18.

At the end of the tube unit 19, there is provided the above-described scope connector 41, which is detachably connected to the AWS unit 4.

The insertion portion 21 includes the hard front end portion 24 arranged at the front end of the insertion portion 21, freely bendable bending portion 27 provided at the rear end of the front end portion 24, and an elongated flexible portion (corrugated tube portion) 53 ranging from the rear end of the bending portion 27 to the operation portion 22. At a plurality of locations, and specifically at two locations, on the way along the flexible portion 53, there are provided rigidity varying actuators 54A and 54B, referred to as electric conducting polymer artificial muscles (hereinafter abbreviated as EPAM) that can be expanded/contracted and also varied in hardness by application of a voltage.

Inside an illumination window provided at the front end portion 24 of the insertion portion 21, as illumination means, e.g., a light-emitting diode (hereinafter abbreviated as a LED) 56 is affixed. The illumination light by the LED 56 is emitted in the forward direction through an illumination lens integrally attached to the LED 56, and illuminates a subject such as an affected area. The LED 56 may be an LED that emits white light. Alternatively, the LED 56 may be constituted of an LED for red light, LED for green light, and LED for blue light, that emit light in their respective wavelength ranges out of red, green, and blue light. However, the light emitting element is not limited to the LED 56, but the light emitting element can also be constituted by a laser diode (LD).

An objective lens (not shown) is affixed to the observation window arranged adjacently to the illumination window, and at the image forming position thereof, the CCD 25 having therein a variable gain function is arranged, thereby forming image pickup means for picking up an image of a subject. The CCD 25 in this embodiment incorporates the variable gain function in the CCD element itself, and can easily vary the gain of a CCD output signal up to about several hundred times, so that a bright image that is low in the S/N ratio drop can be achieved even under the illumination light by the LED 56. Also, because the LED 56 is superior in luminous efficiency to a lamp, a temperature rise in the area in the vicinity of the LED 56 can be suppressed.

One end of each of the signal lines is connected to a respective one of the LED 56 and CCD 25, and each of the signal lines is inserted through the insertion portion 21. The other end of each of the signal lines is disposed, e.g., inside the operation portion 22, and connected to a control circuit 57 that performs concentrated control processing (intensive control processing).

Within the insertion portion 21, a plurality of UPD coils 58 (serving as insertion portion shape detecting device) are arranged at predetermined spacings along the longitudinal direction. The signal line connected to each of the UPD coils 58 is connected to the control circuit 57 via a UPD coil drive unit 59 provided in the operation portion 22.

At four locations along the peripheral direction, inside an external sheath of the bending portion 27, there is an angle actuator 27a formed by arranging the EPAM in the longitudinal direction of the bending portion 27. The angle actuator 27a as well as the rigidity varying actuators 54A and 54B are connected to the control circuit 57 via respective signal lines.

The EPAM used for the angle actuator 27a and rigidity varying actuators 54A and 54B can be contracted in the thickness direction and expanded in the longitudinal direction e.g., by attaching electrodes on both surfaces of a plate-shaped EPAM and applying a voltage thereto. In this EPAM, for example, the strain amount can be vary in proportion to substantially the square of the electric field strength E generated by an applied voltage. When the EPAM is used for the angle actuator 27a, forming the EPAM into a wire shape or the like, and expanding one side of the wire while contracting the other side, allows the bending portion 27 to bend performing the same function as that of a common wire. Also, by these expansion and contraction, the hardness of the bend portion 27 can be variably adjusted. The rigidity varying actuators 54A and 54B variably adjusts the hardness of the bending portion 27 by taking advantage of the above-described function.

An air/water feed pipe line 60a and suction pipe line 61a are arranged through the insertion portion 21, and the rear end of the insertion portion 21 constitutes a pipe line connector portion 51a that opens in the connector portion 51. A tube connector 52a in the overall connector portion 52 at the base end of the tube unit 19 is detachably connected to the pipe line connector portion 51a.

The air/water feed pipe line 60a is connected to the air/water feed pipe line 60b arranged through the tube unit 19. The suction pipe line 61a is connected to a suction pipe line 61b, as well as branches off in the tube connector 52a and opens to the outside, thereby communicating with a treatment tool insertion port (hereinafter abbreviated as a forceps port) 62 that allows a treatment tool such as a forceps to be inserted. This forceps port 62 is blocked when it is not used, by a forceps plug 62a.

The proximal sides (rear ends) of these air/water feed pipe line 60b and suction pipe line 61b constitute an air/water feed mouthpiece 63 and suction mouthpiece 64, respectively, in the scope connector 41.

The air/water feed mouthpiece 63 and suction mouthpiece 64, respectively, are connected to an air/water feed connector and suction connector of the AWS adapter 42. As shown in FIG. 6, inside the AWS adapter 42, the air/water feed connector branches off into an air feed pipe line and water feed pipe line.

The air feed pipe line is connected to an air/water feed pump 65 inside the AWS unit 4 via an electromagnetic valve B1, while the water feed pipe line is connected to a water feed tank 48. The water feed tank 48 is also connected to the air/water feed pump 65 via an electromagnetic valve B2 on the way.

The air/water feed pump 65 and electromagnetic valves B1 and B2 are connected to an AWS control unit 66 by control lines (drive lines), and the opening/closing of the electromagnetic valves B1 and B2 is controlled by the AWS control unit 66 so as to be able to perform air feed and water feed. Here, the AWS control unit 66 also performs control of suction operations under open/close control by the pinch valve 45.

As shown in FIG. 7, the operation portion 22 of the endoscope body 18 has a holding portion 68 to be gripped by the operator. At the periphery of the holding portion 68 including it, for example, three scope switches SW1, SW2, and SW3 for performing remote control operations such as release and freeze, are arranged along the longitudinal axis of the operation portion 22, and they are each connected to the control circuit 57.

On a slope portion Sa obliquely formed, as a top surface, oppositely to locations where the SW1, SW2, and SW3 are disposed, a waterproof-structured trackball 69 by which the operator performs an angle operation (bending operation) or setting of another remote control operation by making a changeover, is arranged at a location allowing the operator to operate the trackball 69 by the operator's hand that is holding it.

Figure 8:
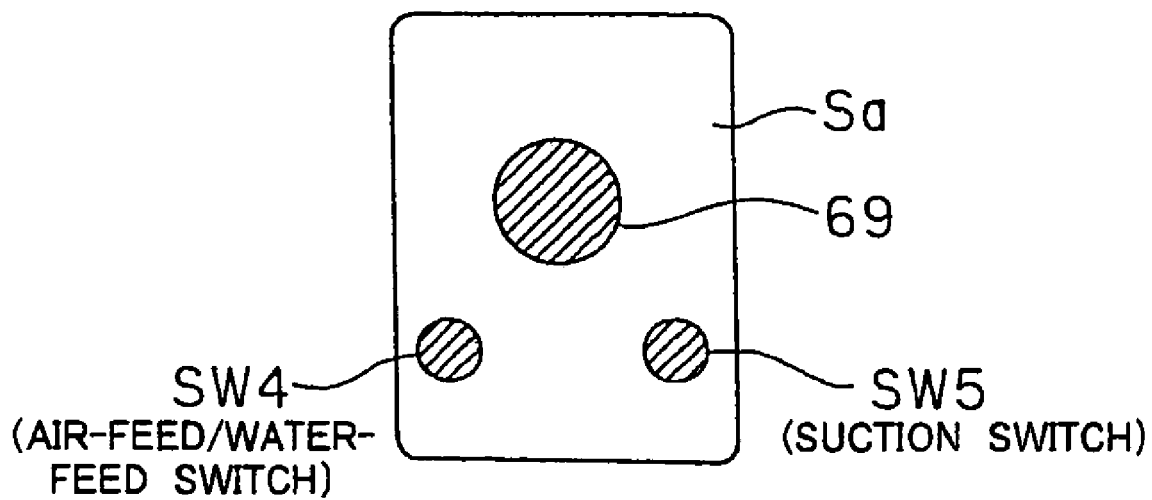
FIG. 8 is an arrow view of a trackball and others provided in an operation portion, as viewed in the direction of an arrow C in FIG. 7.

FIG. 8 is an arrow view along a C direction in FIG. 7. As shown in FIG. 8, on both sides of the trackball 69 on the slope portion Sa, two scope switches SW4 and SW5 are disposed at locations such as to be bilaterally symmetric relative to the longitudinal axis of the operation portion 22. Typically, functions of air/water feed switch and suction switch are allocated to the scope switches SW4 and SW5, respectively.

Letting the surface as the operation portion 22 of the endoscope 3 is viewed along the direction of the arrow C in FIG. 7 be a front, the trackball 69 is located on a center line in the longitudinal direction of the operation portion 22 or insertion portion 21, and the two scope switches SW 4 and SW5 are disposed at locations that are bilaterally symmetrical relative to the center line, as well as the scope switches SW1, SW2, and SW3 are disposed at the rear side of the front along the center line.

In this manner, in this operation portion 22, the various operating means including the trackball 69 are arranged at the locations bilaterally symmetric relative to the center axis in the longitudinal direction, and hence, when the operator performs an operation while holding the holding portion 68 of the operation portion 22, it is possible to secure equally satisfactory operability irrespective of whether the operator performs an operation by holding the holding portion 68 with the operator's left hand, or right hand.

The trackball 69 and scope switches SW4 and SW5 are also connected to the control circuit 57. The trackball 69 and the scope switches SW1 to SW5 correspond to the angle/remote control operator 28 in FIG. 3.

Also, a power supply line 71a extended from the control circuit 57 is electrically connected in a contactless manner with a power supply line 73a that is arranged through the tube unit 19 via a contactless transmission portion 72a formed in the connector portion 51 and overall connector portion 52. The power supply line 73a is connected to an electric connector 74 having a power source and signal contact at the scope connector 41. Here, the side of the connecter portion 51 in the contactless transmission portion 72a is referred to as, e.g., a contactless transmission unit 51b.

Figure 12:
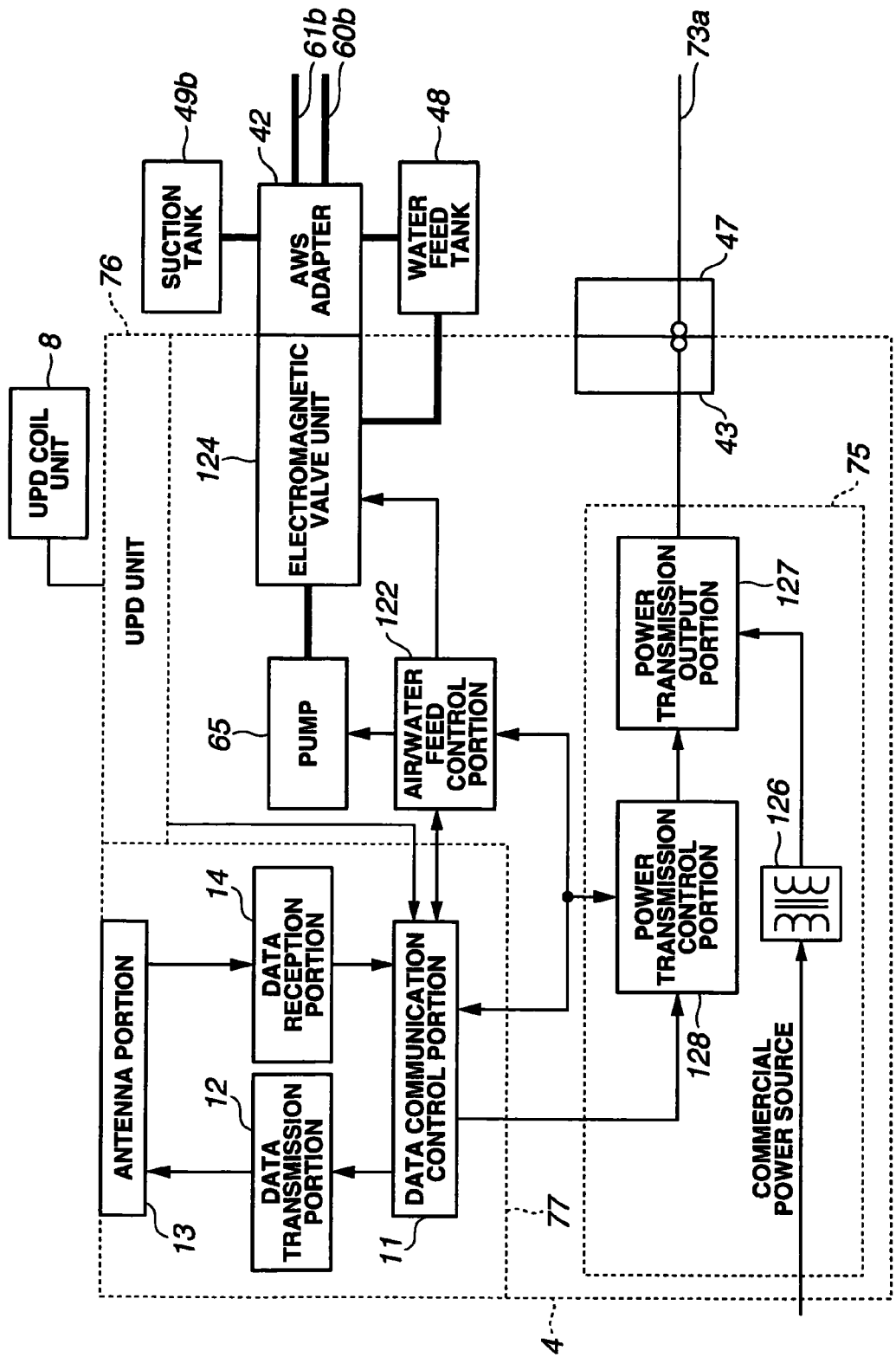
FIG. 12 is a block diagram showing the configuration of an electrical system in the AWS unit.

A user connects the scope connector 41 to the AWS unit 4, and thereby the power supply line 73a is connected to a power source unit 75 via the electricity connector 43 of the AWS unit 4 as shown in FIGS. 6 and 12. A transmission/reception unit 77 is connected to an antenna for performing radio wave transmission/reception by radio.

As shown in FIG. 7, in the endoscope 3 according to this embodiment, radio is used as means for transmitting image data picked up by the CCD 25. To this end, an antenna portion 141 is provided, e.g., inside the rear end (upper end) of the operation portion 22.

Figure 9:
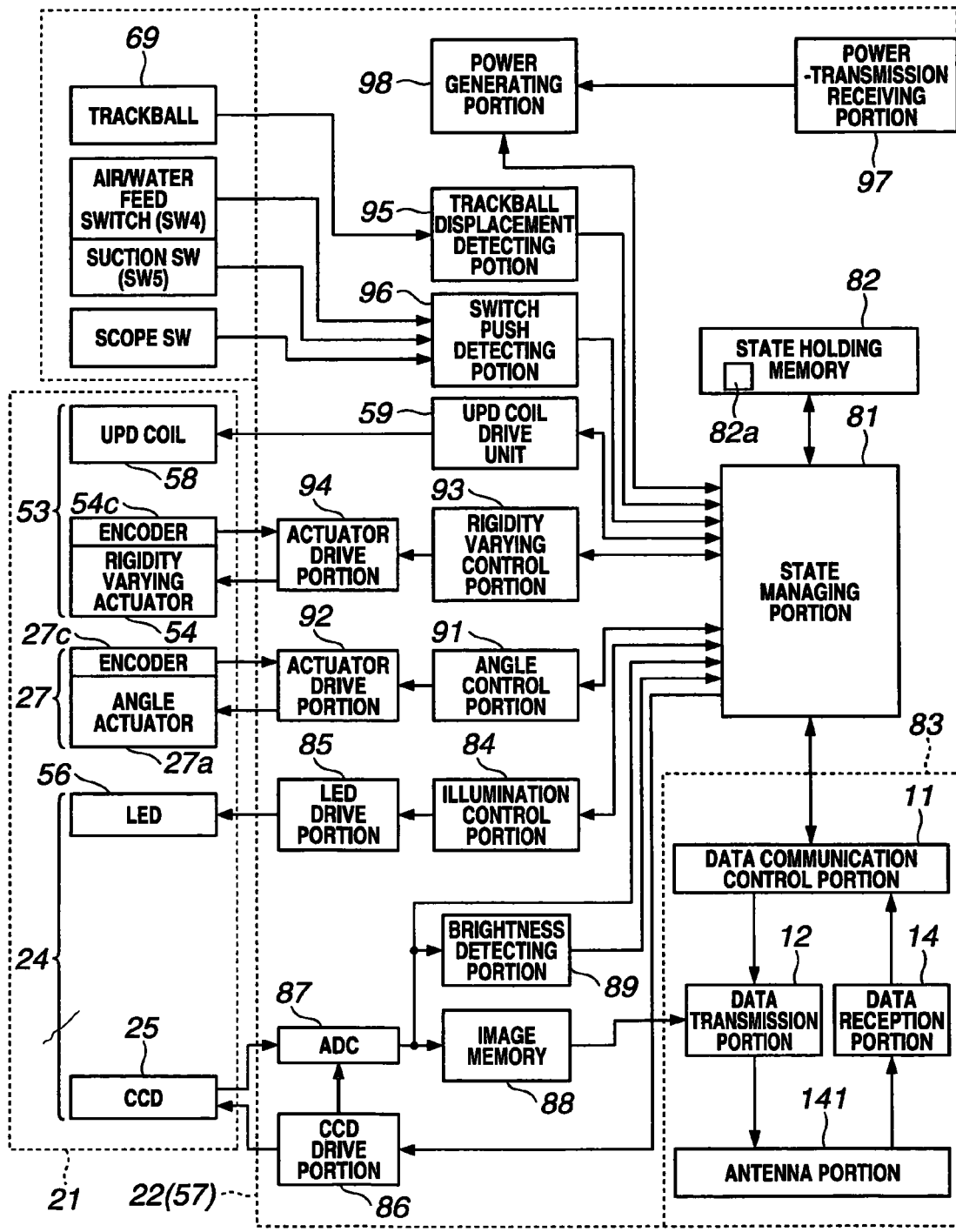
FIG. 9 is a block diagram showing the configuration of an electrical system in configuration components provided in the endoscope.

In this embodiment, as described in FIG. 9 of its internal configuration, by using a configuration in which the control circuit 57 concentratedly controls or manages various operating means and image pickup means, it suffices for the tube unit 19 only to have the power supply line 73a as an electric signal line outside the pipe lines. The transmission of signals to/from the outside is performed by radio via the antenna portion 141.

Even if functions provided for the endoscope 3 are changed, the power supply line 73a can be used just as it is, without any change.

Furthermore, one of the features of the endoscope 3 according to this embodiment lies in that the endoscope body 18 is configured to be detachably connected to the tube unit 19 in a contactless manner.

FIG. 9 shows the configurations of the control circuit 57 etc. arranged in the operation portion 22 of the endoscope body 18, and an electric system in main components arranged in various portions of the insertion portion 21.

At the front end portion 24 of the insertion portion 21, shown in a lower left portion in FIG. 9, there are provided the CCD 25 and LED 56, and at the bending portion 27 shown thereabove in FIG. 9, there are provided the angle actuator (specifically, EPAM in this embodiment) 27a and an encoder 27c.

In the flexible portion 53, there are provided a rigidity varying actuator 54 (specifically, rigidity varying actuators 54A and 54B by EPAM are used in this embodiment, but here, they are represented merely by hardness adjustment actuator 54, for the sake of simplification), as well as an encoder 54c. Also, the flexible portion 53 has UPD coils 58.

On the surface of the operation portion 22, shown above the flexible portion 53 of the insertion portion 21, there are provided the trackball 69, the air/water feed switch SW (SW4), suction SW (SW5), and scope SWs (SW1 to SW3). As will be described later, the trackball 69 is used for, e.g., selection setting for making a selection between the angle operation and other functions.

These components shown at the left side of FIG. 9 are connected to the control circuit 57 provided in the operation portion 22 shown on the right side of these components in FIG. 9, via a signal line. Here, the UPD coil drive unit 59 is located inside the operation portion 22. The control circuit 57 performs drive control with respect to these functions, signal processing, or the like.

The control circuit 57 has a state managing portion 81, constituted of a CPU and the like that manage control states. The state managing portion 81 is connected to a state holding memory 82 for holding (storing) a state of each portion. The state holding memory 82 has a program holding memory 82a, whereby, even if some of components shown in FIG. 9 are changed, (the CPU of) the state managing portion 81 can perform control (management) corresponding to the changed configurations, by rewriting program data as control information to be stored in the program holding memory 82a.

The state holding memory 82 or at least the program holding memory 82a is constituted of e.g., a flash memory, EEPROM, or the like that is nonvolatile and electrically rewritable, so that the change of program data can be easily performed via the state managing portion 81.

For example, a command for changing program data is sent to the state managing portion 81 via the antenna portion 141, namely, via a transmission/reception unit 83 by radio, and after having sent the command, program data to be rewritten is transmitted, whereby the change of program data can be performed. Moreover, the version upgrade or the like can also be easily performed via the antenna portion 141.

The arrangement may also be such that e.g., model information specific to the endoscope 3, or individual information corresponding to usage conditions are written into the state holding memory 82 as will be described below, and held, whereby these pieces of information can be effectively used.

Specifically, the state holding memory 82 holds, for example, model information on the endoscope 3 (e.g., information on the kind of the CCD 25, the length of the insertion portion, etc), as well as maintains individual information on the endoscopes 3, mutually different depending on usage conditions of an endoscope examination or the like (e.g., information on a usage time (the total or accumulated usage time for endoscope examinations), number of cleaning operations, adjustment value, maintenance history, etc). These pieces of information are utilized for the determination of a system operation or information presentation to users.

These pieces of information also allows the endoscope system control apparatus 5 or a cleaning apparatus (not shown) to be extraneously edited.

Thereby, the state holding memory 82 doubles in function as the conventional scope ID, so that the combined use of these two functions allows an effective use of information (data) provided to the scope ID.

Furthermore, the presence of the state holding memory 82 eliminates the need to separately provide the scope ID, and makes it possible to provide functionality higher than that of the existing scope ID, as well as to perform appropriate setting, adjustment, management, and processing in a more detailed manner.

The state managing portion 81 (in this embodiment) is connected to a wireless type transmission/reception unit 83 that performs communications between the AWS unit 4 and the endoscope system control apparatus 5 (since this transmission/reception unit 83 corresponds to the case in FIG. 2A, its components are designated by the reference numerals shown in FIG. 2A, with the exception that an antenna portion is designated by reference numeral 141).

Also, the state managing portion 81 controls an LED drive portion 85 via an illumination control portion 84 for controlling illumination. And the LED drive portion 85 is controlled by the illumination control portion 84. The LED drive portion 85 applies a LED drive signal for causing the LED 56 emit light, to the LED 56 which is illumination means.

By this light emission of LED 56, an illuminated subject such as an affected area is formed at a image pickup surface of the CCD 25 disposed at an image forming position by an objective lens (not shown) attached at the observation window, and then optoelectronically converted by the CCD 25.

Upon the application of a CCD drive signal from a CCD drive portion 86 controlled by the state managing portion 81, the CCD 25 outputs signal charges that have been optoelectronically converted and stored, as image pickup signals. After the image pickup signals have been converted from analog signals into digital signals by an A/D converter (hereinafter abbreviated as ADC) 87, they are inputted into the state managing portion 81, and the digital signals (image data) are stored in a memory 88. The image data in the memory 88 is sent to the data transmission portion 12 of the transmission/reception unit 83.

Then, the image data in the memory 88 is transmitted from the antenna portion 141 to the endoscope system control apparatus 5.

The output signals from the above-described ADC 87 are sent to a brightness detecting portion 89, and information on brightness of the images, detected by the brightness detecting portion 89 is sent to the state managing portion 81. By this information, the state managing portion 81 performs dimming control so that illumination light by the LED 56 becomes a proper brightness, via the illumination control portion 84.

Furthermore, the state managing portion 81 controls an actuator drive portion 92 via an angle control portion 91, and performs management of driving the angle actuator (EPAM) 27a by the actuator drive portion 92. Here, the drive amount of the angle actuator (EPAM) 27a is detected by the encoder 27c, and controlled so that the drive amount conforms to a value corresponding to an instruction value.

Also, the state managing portion 81 controls an actuator drive portion 94 via a hardness adjustment control portion 93, and performs management of driving the rigidity varying actuator 54 by this actuator drive portion 94. Here, the drive amount of the rigidity varying actuator 54 is detected by the encoder 54c, and controlled so that the drive amount becomes a value corresponding to an instruction value.

To this state managing portion 81, an operation signal corresponding to an operation amount from the trackball 69 or the like provided in the operation portion 22 is inputted via a trackball displacement detecting portion 95.

The switch pushing operation such as a turn-on by the air/water feed SW, suction SW, or scope SW is detected by a switch push detecting portion 96, and the detected information is inputted into the state managing portion 81. Here, because the EPAM has a property of generating an electromotive force under deformation caused by an extraneous force, an EPAM arranged oppositely to the EPAM that is driven may be used as an encoder.

The control circuit 57 has a power-transmission receiving portion 97 and power generating portion 98. To be specific, the power-transmission receiving portion 97 is the contactless transmission portion 72a at the operation portion 22. AC power transmitted to the power generating portion 98 is converted into DC power at the power generating portion 98. The DC power generated by the power generating portion 98 supplies each portion inside the control circuit 57 with power necessary for its operation.

Figure 10:
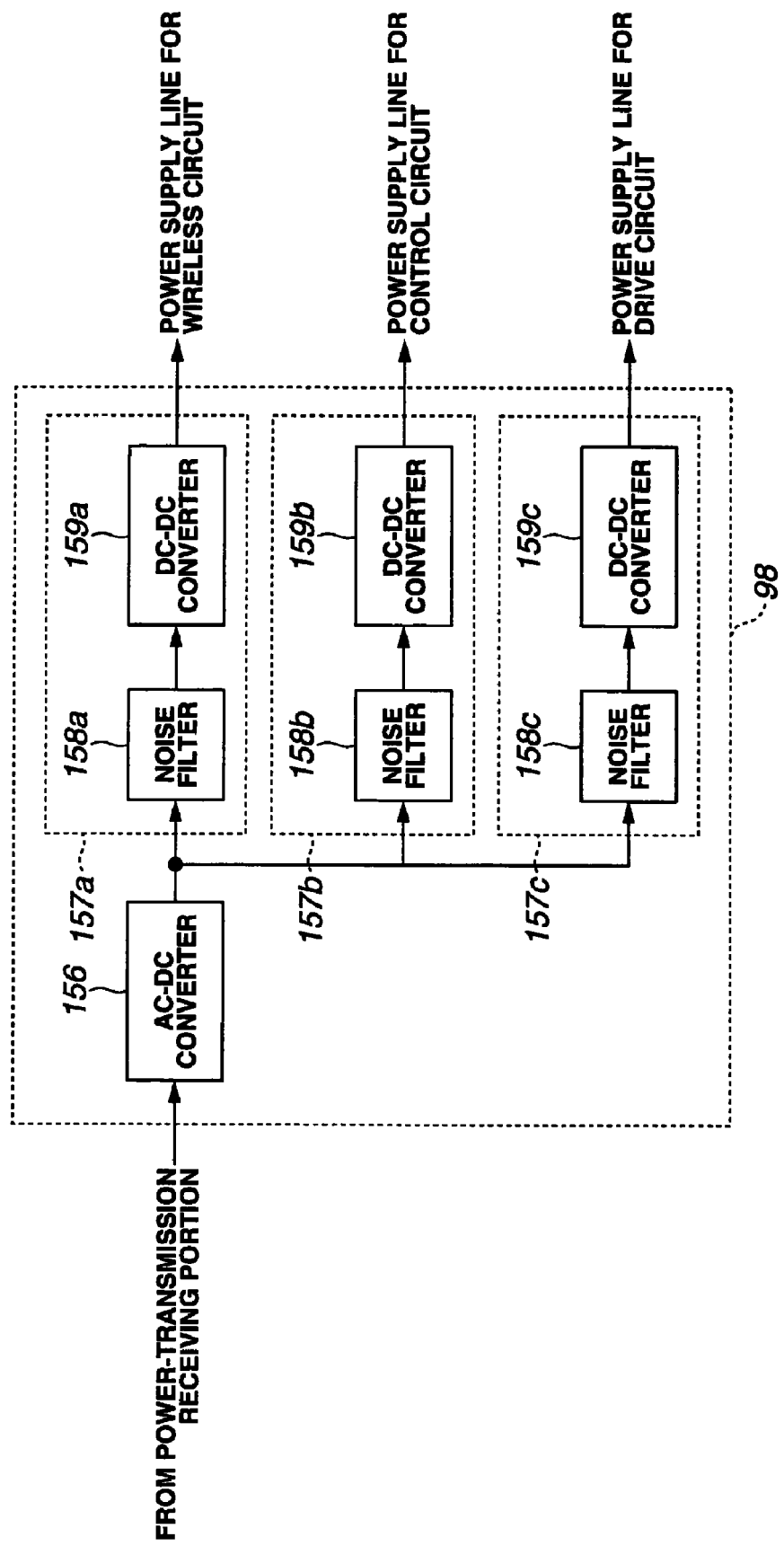
FIG. 10 is a block diagram showing the configuration of a voltage generating portion.

In this case, the power generating portion 98 has a configuration as shown in FIG. 10. The AC power that has been transferred by the power-transmission receiving portion 97 is firstly converted into DC power by an AC-DC converter 156, and is then supplied to three DC power generating portions: a wireless circuit power generating portion 157a, control circuit power generating portion 157b, and drive circuit power generating portion 157c, respectively.

The wireless circuit power generating portion 157a, control circuit power generating portion 157b, and drive circuit power generating portion 157c, respectively, are constituted of noise filters 158a, 158b, and 158c; and DC-DC converters 159a, 159b, and 159c. The DC powers generated by the DC-DC converters 159a, 159b, and 159c are supplied to three blocks: a wireless related circuit system, control related circuit system, and drive related circuit system for driving the image pickup means, via a wireless circuit power supply line, control circuit power supply line, and drive circuit power supply line, respectively.

In this embodiment, with respect to such three blocks: wireless related circuit system, control related circuit system, and drive related circuit system, respectively, there are provided the wireless circuit power generating portion 157a, control circuit power generating portion 157b, and drive circuit power generating portion 157c, which are independent of one another, and simultaneously, noise filters 158a, 158b, and 158c, respectively, are provided in order to prevent noises unnecessary for respective operations from intruding. Therefore, each of the circuits can perform a stable operation without being affected by noise.

Figure 11:
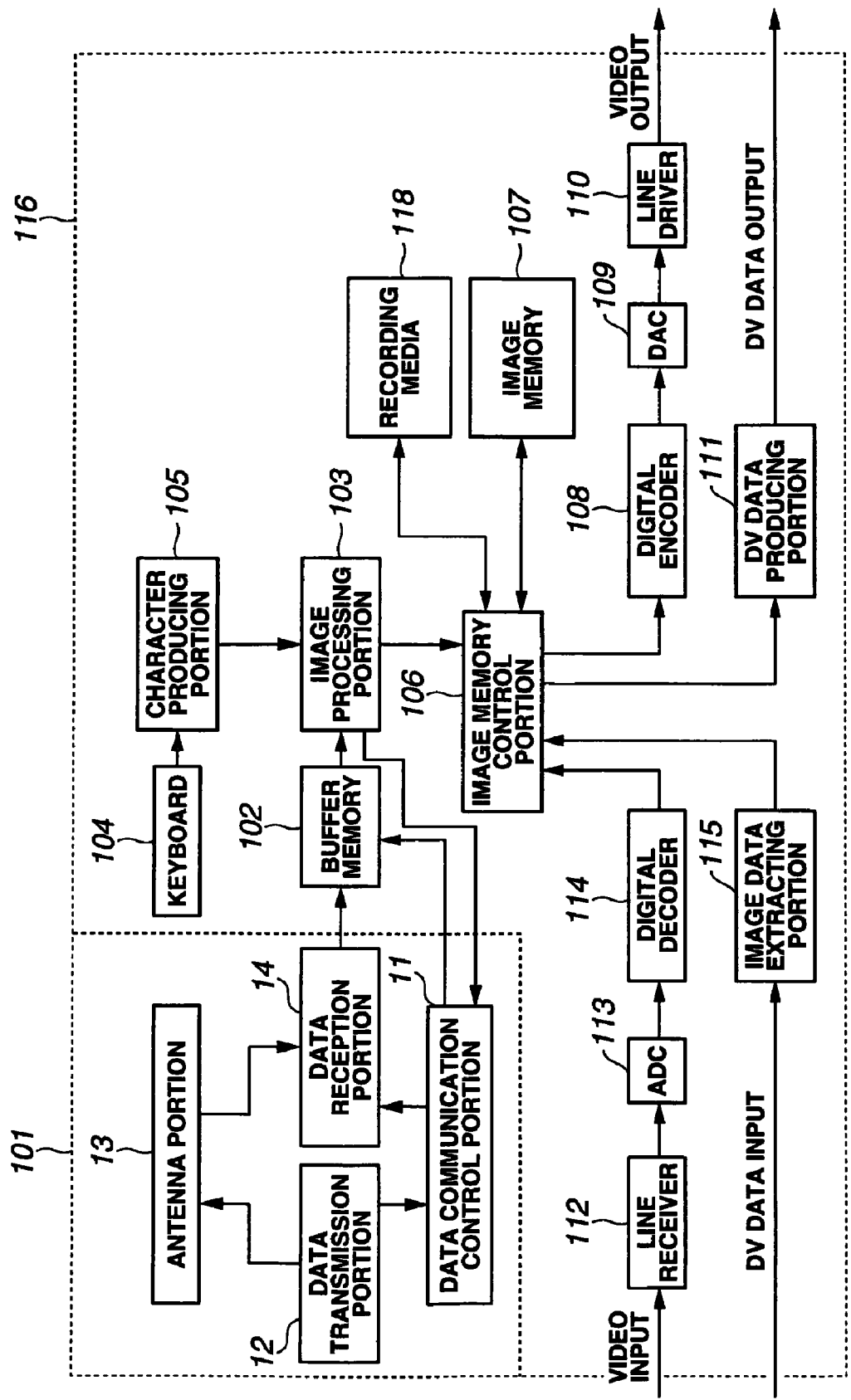
FIG. 11 is a block diagram showing the configuration of an electrical system in the main portion of an endoscope system control apparatus.

FIG. 11 shows the internal configuration of each of a transmission/reception unit 101 and an image processing unit 116 shown in FIG. 6, in the endoscope system control apparatus 5.

The endoscope system control apparatus 5 has, for example, the wireless type transmission/reception unit 101. Data such as image signals transmitted from the endoscope 3 or AWS unit 4 by radio is captured by the antenna portion 13, and sent to the data reception portion 14. After having been amplified, the data is subjected to demodulation processing. The data reception portion 14 is operationally controlled by the data communication control portion 11, and the received data is sequentially stored in a buffer memory 102.

The image data in the buffer memory 102 is sent to an image processing portion 103 for performing image data processing. To this image processing portion 103, an input from a character producing portion 105 that generates character information by a key input from a keyboard 104 is also inputted besides the image data from the buffer memory 102, whereby the character information can also be superimposed on the image data.

The image processing portion 103 sends inputted image data (and the like) to an image memory control portion 106, and temporarily stores it in an image memory 107 via the image memory control portion 106, as well as records it on a recording media 118.

The image memory control portion 106 reads the image data that has been temporarily stored in the image memory 107, and sends it to a digital encoder 108. Then, the digital encoder 108 encodes the image data in a predetermined image mode, and outputs it to a D/A converter (hereinafter abbreviated as DAC) 109. The DAC 109 converts digital video signals into analog video signals. Furthermore, these analog video signals are outputted from a video output terminal through a line driver 110 to the observation monitor 6, and an image corresponding to the video signals is displayed on the observation monitor 6.

Also, the image data that has been temporarily stored in the image memory 107 is read and inputted also to a DV data producing portion 111. DV data is generated by this DVD data generating portion 111, and the DV data is outputted from a data output terminal.

The endoscope system control apparatus 5 has a video input terminal and DV data input terminal. Video signals inputted from the video input terminal are converted into digital signals through a line receiver 112 and ADC 113, and after having been demodulated by a digital decoder 114, they are inputted into the image memory control portion 106.

Also, DV data inputted from the DV data input terminal, image data is extracted (decoded) by an image data extracting portion 115, and inputted into the image memory control portion 106.

Even with respect to the video signals (image data) inputted from the video input terminal or DV data input terminal, the image memory control portion 106 temporarily stores them in the image memory 107, records them on the image memory 107, or outputs them from the video output terminal to the observation monitor 6.

In this embodiment, image data picked up by the CCD 25 of the endoscope 3, and UPD image data generated by an UPD unit 76 are inputted into the endoscope system control apparatus 5 by radio. The endoscope system control apparatus 5 converts these pieces of data into a predetermined video signals, and outputs them on the observation monitor 6. The endoscope system control apparatus 5 may receive UPD coil location data instead of the UPD image data and generate the UPD image data inside the image processing portion 103.

FIG. 12 shows the internal configuration of the AWS unit 4.

UPD image data that has transmitted from the endoscope 3 by radio and that has been detected by the UPD coils 58 is inputted into the UPD unit 76 via the transmission/reception unit 77.

The UPD unit 76 generates UPD image data, and transmits it from its antenna portion 13 to the antenna portion 13 of the endoscope system control apparatus 5.

Also, even when the air/water feed switch or suction switch provided in the operation portion 22 of the endoscope 3 is operated, its instruction signal is inputted into the AWS control unit 66 via the transmission/reception unit 77. An air/water feed control portion 122 in the AWS control unit 66 controls operations of the pump 65 and an electromagnetic valve unit 124 in response to information on the operations.

To the electromagnetic valve unit 124, the air/water feed pipe lines 60b and 61b are connected via the AWS adapter 42. To the electromagnetic valve unit 124 and AWS adapter 42, a water feed tank 48 is connected. Also, to the AWS adapter 42, a suction tank 49b is connected.

Commercial power is supplied to the AWS unit 4, and the commercial power is sent to a power transmission output portion 127 via an insulating transformer 126. The power transmission output portion 127 supplies AC power insulated from the commercial power, from the electricity connector 43 to a power supply line 73a of the endoscope 3, the power supply line 73a being connected to the electricity connector 43.

In the above-described power transmission output portion 127, its power transmission output is controlled by a power transmission control portion 128 connected to the data communication control portion 11.

Figure 13A:
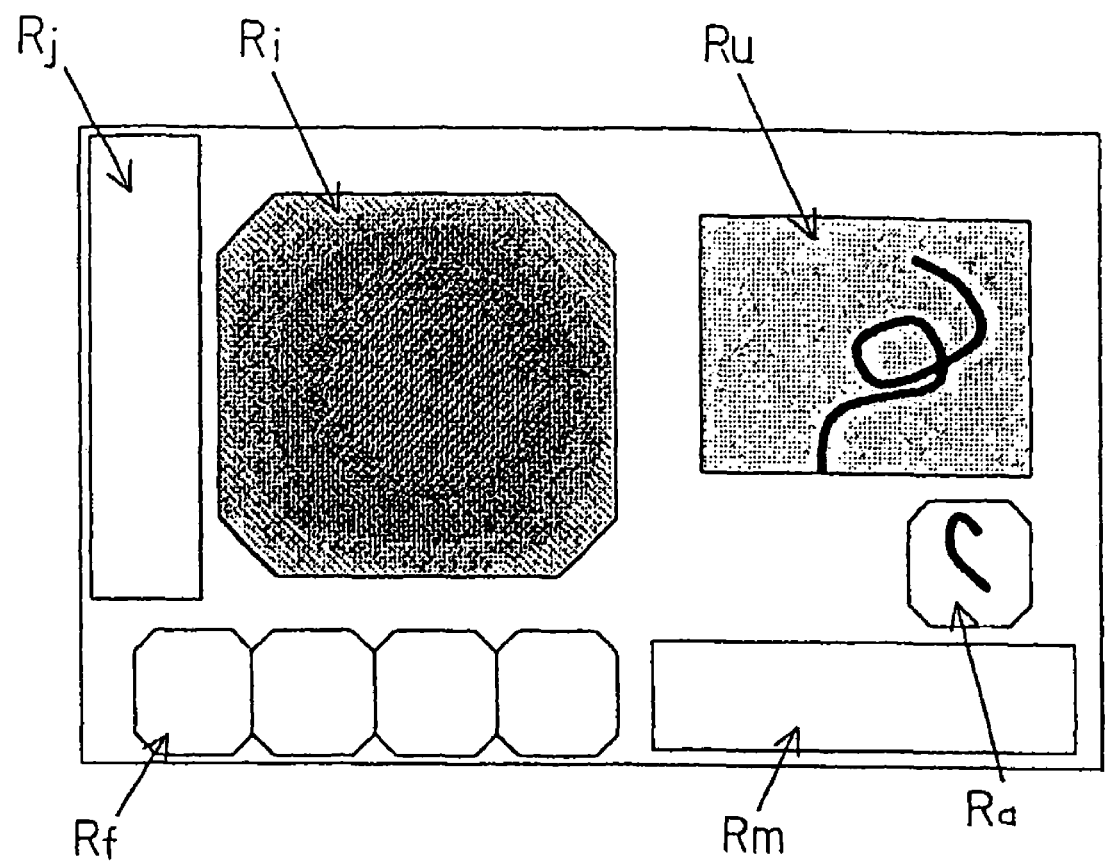
FIGS. 13A to 13C are each a representation of a display example of on a monitor, wherein FIGS. 13A, 13B, and 13C, respectively, show an endoscope image, main menu, and function allocation to function switches.

In the endoscope system 1 according to the present invention, when the power is turned on, various images are displayed on the observation monitor 6 as shown in FIG. 13A for example. In this case, there are provided a information display region Rj that displays patient information or the like, display region Ri for an endoscope image, display region Ru for an UPD image, display region Rf for a freeze image, display region Ra for an angle shape, and besides a menu display region Rm for displaying a menu. Here, the display region Ra for an angle shape detects an angle operation amount of the angle actuator 27a by the encoder 27c, and displays the angle shape in this case.

Figure 13B:
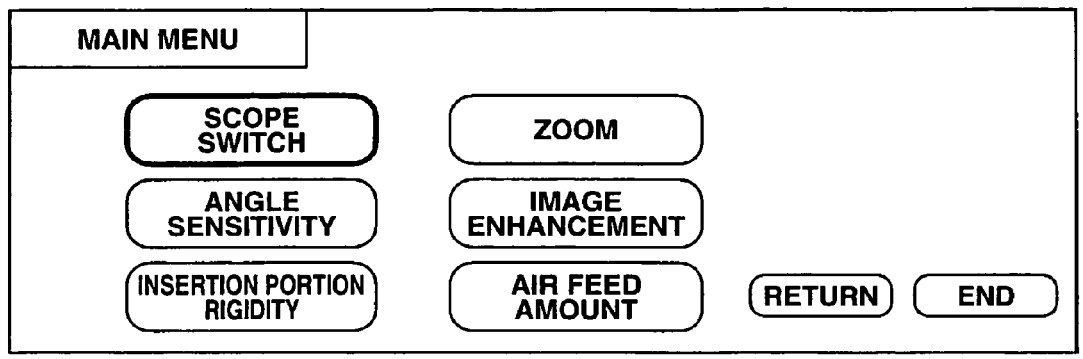

As a menu displayed on the menu display region Rm, a main menu shown in FIG. 13B is displayed. When operation instructions for a scope switch, angle sensitivity, insertion portion hardness, zoom, image enhancement, air feed amount are performed, followed by an operation instruction for returning to the previous screen, an item of "end" showing an operation instruction for finishing the menu is displayed on the main menu.

Figure 13C:
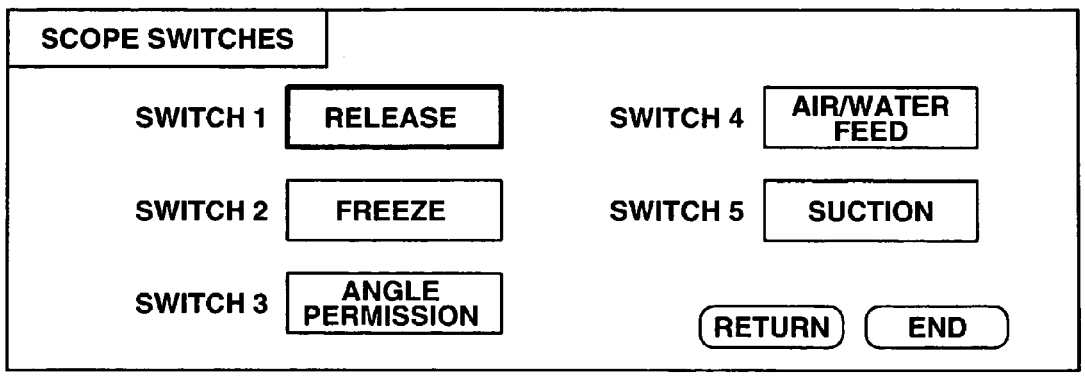

Then, when the user moves to select the item of scope switch in a selection frame by an operation of the trackball 69 or the like, the frame of the scope switch item is display thick, thereby indicating that this item has been selected. Furthermore, by pushing the trackball 69 to perform determination operation, it is possible to selectively set functions to be allocated to five scope switches SW1 to SW5 as shown in FIG. 13C.

Next, operations of the endoscope system 1 with such arrangements will be described.

As a preparation to the execution of an endoscope examination, firstly the overall connector portion 52 on the side of the disposable type tube unit 19 is connected to the connector portion 51 of the operation portion 22 in the endoscope body 18. In this case, transformers (not shown) forming the contactless transmission portion 72a are electromagnetically connected with each other in a mutually insulated and waterproof state. By this connection, the preparation of the endoscope 3 is completed.

Then, the scope connector 41 of the tube unit 19 is connected to the electricity connector 43 of the AWS unit 4. In this portion, connections of various pipe lines and power supply lines are completed by one time connecting operation, namely, one touch connection. There is no need to perform connections of various pipe lines and connections of electric connectors every time occasion demands, unlike conventional endoscope systems.

The user connects the AWS unit 4 to the UPD coil unit 8, and connects the endoscope system control apparatus 5 to the observation monitor 6. Also, as necessary, by connecting the endoscope system control apparatus 5 to the image recording unit 7 or the like, the setup of the endoscope system 1 is completed.

Next, the AWS unit 4 and endoscope system control apparatus 5 are powered-on. Thereupon, each portion in the AWS unit 4 enters an operating state, and the power source unit 75 becomes ready to supply power to the endoscope 3 via the power supply line 73a.

Operation during the activation of the AWS unit 4 and endoscope 3 in this case will be described with reference to FIGS. 14 and 15.

Figure 14:
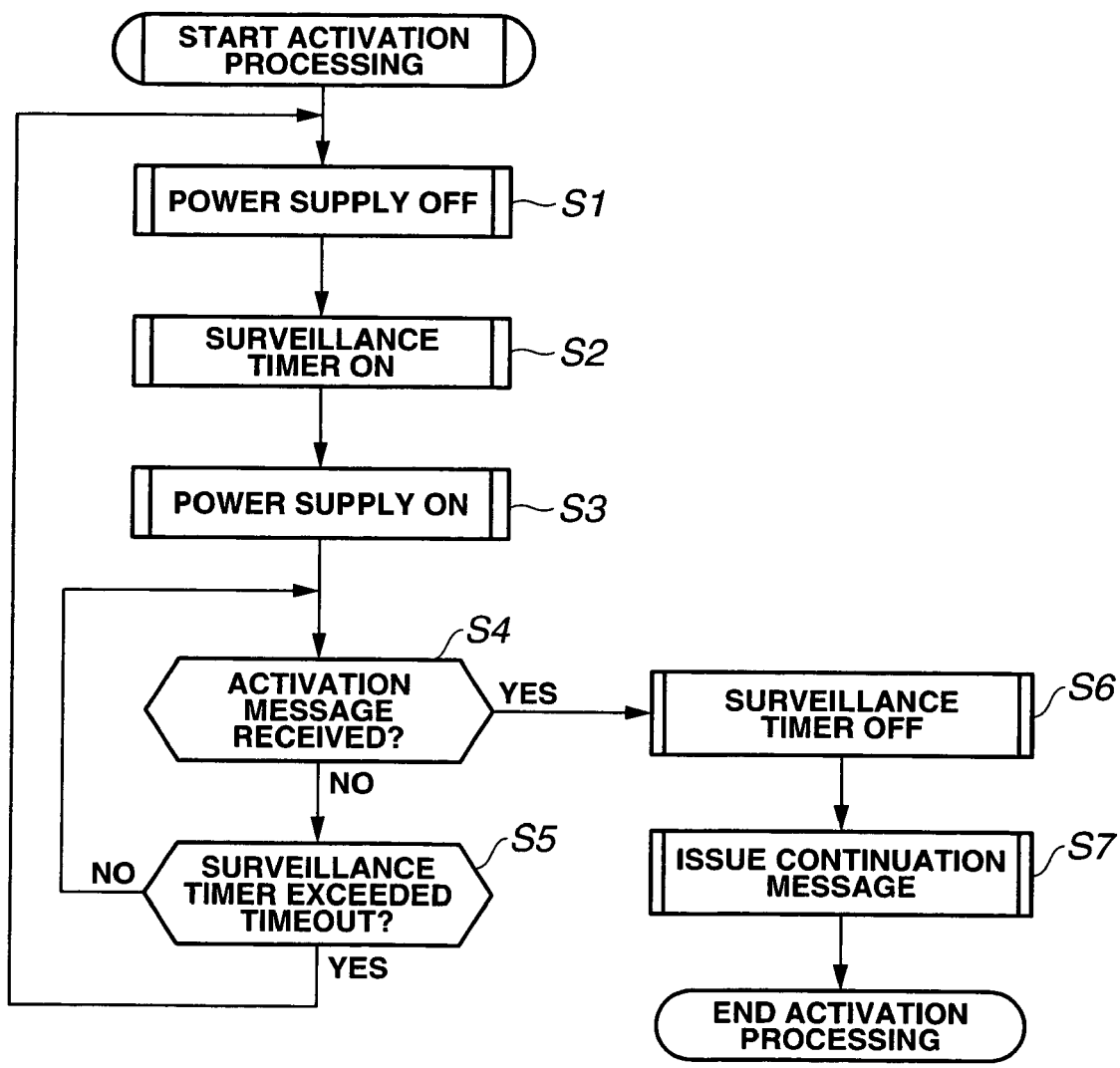
FIG. 14 is a flowchart showing operational contents of activation processing with respect to the AWS unit.
Figure 15:
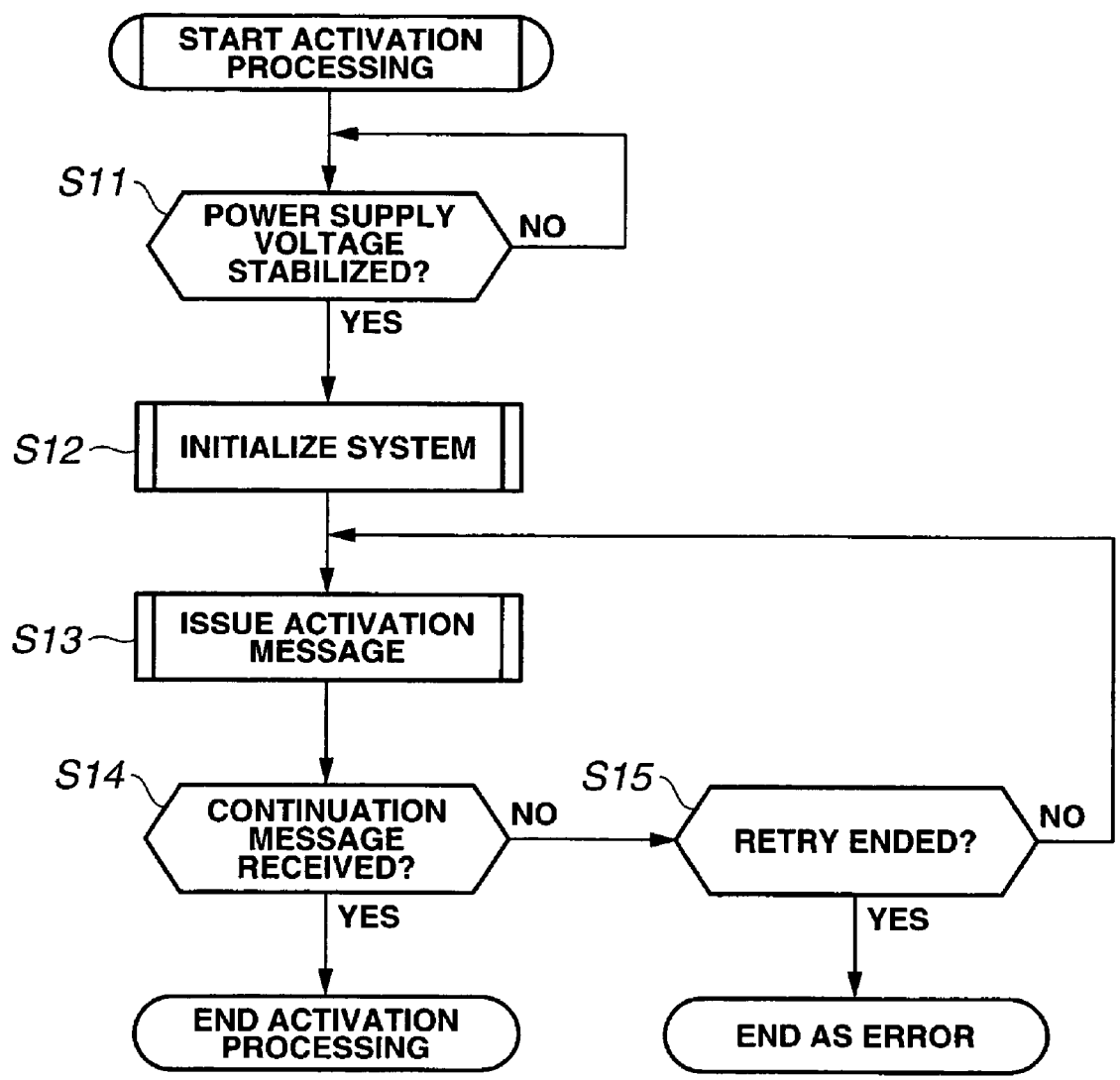
FIG. 15 is a flowchart showing operational contents of activation processing with respect to the endoscope.

Upon starting of activation processing, in a first step S1, the power transmission control portion 128 in the power source unit 75 of the AWS unit 4, shown in FIG. 12, brings the power transmission output portion 127 into a state of stopping power supply, i.e., a power-off state, as shown in FIG. 14.

Then, after a surveillance monitor has been turned on in a step S2, as shown in a step S3, the power transmission output portion 127 is brought into a state of supplying power, i.e., a power-on state. By the power transmission output portion 127 entering the state of supplying power, AC power comes to be supplied to the power generating portion 98 in the control circuit 57 of the operation portion 22, via the power supply line 73a in the tube unit 19, and further through the contactless transmission portion 72a.

Thereafter, as shown in step S4, the power transmission control portion 128 enters a state of waiting for a reception of an activation message from the side of endoscope 3. As shown in step S5, if the power transmission control portion 128 receives no activation message, it makes a determination as to whether the surveillance timer has exceeded a timeout. If not so, the processing returns to the step S4, and if the surveillance timer has exceeded the timeout, the processing returns to the first step S1.

On the other hand, in step S4, if the power transmission control portion 128 has received the activation message before the timeout, it switches off the time measurement of the surveillance timer as shown in step S6. Then, the power transmission control portion 128 issues a continuation message as shown in step S7, thererby ending this activation processing.

On the other hand, by a DC power being supplied to the power generating portion 98, the control circuit 57 is supplied with power necessary for operations in the control circuit 57, and starts activation processing. In a first step S11, the state managing portion 81 shown in FIG. 13 waits for the power supply voltage of the power generating portion 98 to be stabled.

When the power supply voltage has been stabled, in the nest step S12, the state managing portion 81 performs system initialization of each portion of the control circuit 57. After the system initialization, as shown in step S13, the state managing portion 81 wirelessly transmits an activation message to the transmission/reception unit 77 of the AWS unit 4 via the transmission/reception unit 83. The activation message is further transmitted to the power transmission control portion 128.

After the activation message has been transmitted, as shown in step S14, the state managing portion 81 enters a state of waiting for receiving the continuation message from the power transmission control portion 128. If the state managing portion 81 receives the continuation message, it ends the activation processing. On the other hand, if the state managing portion 81 receives no continuation message, as shown in step S15, when a condition for retry end (e.g., condition for a predetermined number of retries) is not reached, the processing returns to the step 13, and issues again the activation message. On the other hand, if the condition for retry end is reached, the processing ends as an error.

Figure 16A:
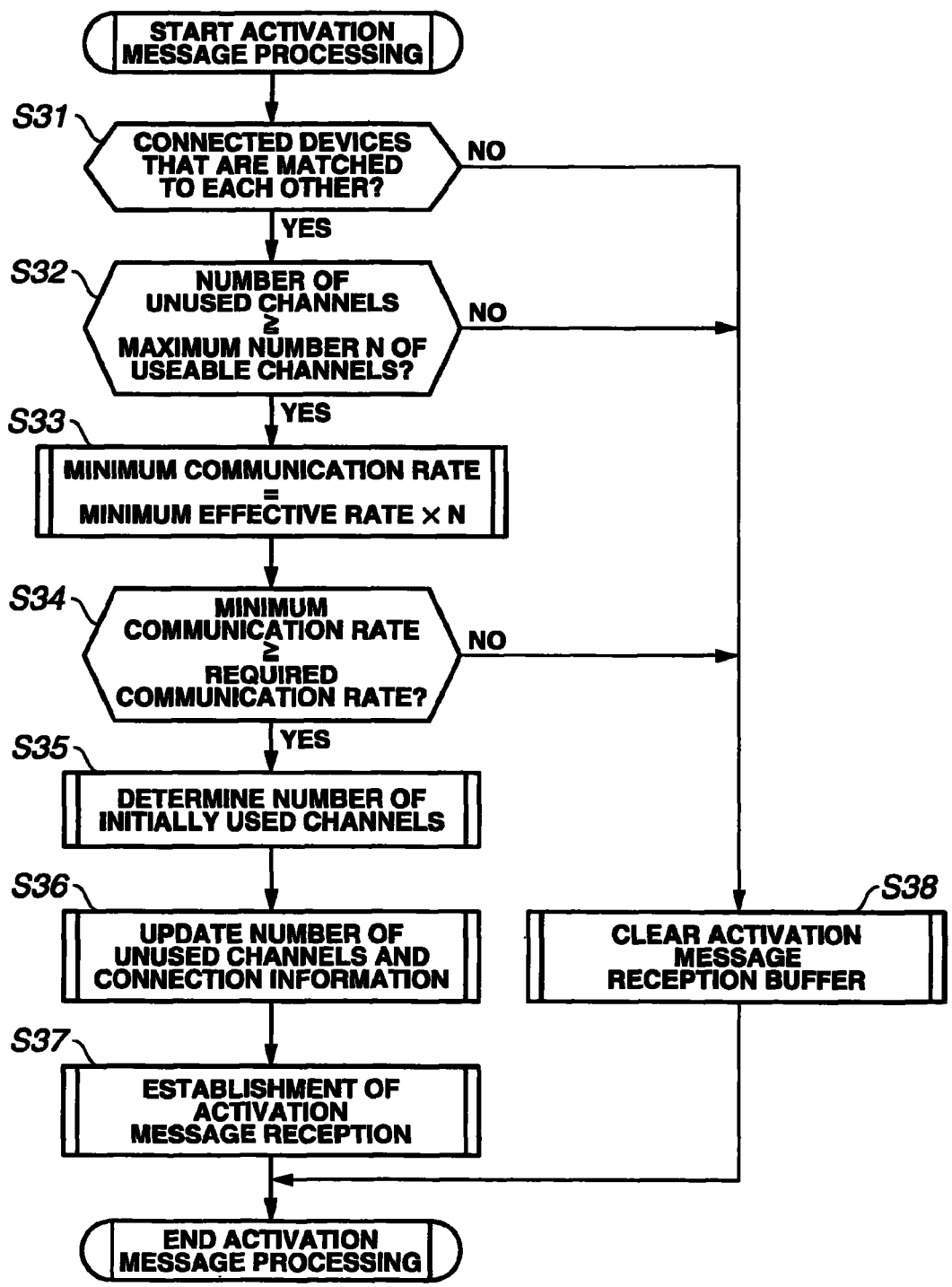
FIG. 16A is a flowchart showing contents of activation processing for determining the possibility of wireless connection during activation.

Also, in processings of the issue and reception of the activation message in the above-described steps S13 and S2, the endoscope 3, AWS unit 4, and endoscope system control apparatus 5 perform connection initialization processing by radio as shown in FIG. 16A, and determine a communication counterpart.

One feature of this embodiment lies in that, giving the highest priority to an effective communication rate by this processing, equipment requiring connections that cannot secure this effective communication rate is prevented from being added in a connection list, whereby a stable data transmission between equipment that is added in the connection list can be performed virtually without being affected by radio wave conditions.

After a target device has been determined as a communication counterpart device, the effective communication rate of the equipment is periodically monitored, and by dynamically change the number of communication channels that is necessary for securing the effective communication rate and that is close to the minimum, on a case-by-case basis, it is possible to reduce radiation electromagnetic waves or power consumption.

With reference to FIG. 16A, this concern will be explained taking the case where the activation message is issued from the endoscope 3 to the AWS unit 4, as an example.

When having received the activation message from the endoscope 3, (the CPU of) the AWS unit 4 determines the target device is a counterpart device connected so as to be matched to it, based on ID information on the endoscope 3, included in the activation message, as shown in step S31.

When issuing of the activation message, the devices issuing the activation message include three pieces of information: (a) the above-described ID information (ID information on the endoscope 3, in the case of the endoscope 3), (b) an required communication rate (i.e., a minimum communication rate necessary for a device transmitting the activation message to transmit data), and (c) a maximum number of usable channels (the maximum value of the number of channels usable for devices transmitting the activation message to perform transmission/reception. These pieces of information are used in the following steps.

In the above-described step S31, if the AWS unit 4 determines that the target device is not a counterpart device connected so as to be matched to it, the processing transfers to step S38, and clears a buffer receiving the activation message, thereby ending the activation message.

On the other hand, in the determination processing in step S31, if the AWS unit 4 determines that the target device is a counterpart device connected so as to be matched to it, the processing advances to step S32, and determines whether the number of unused channels is larger than the maximum number N of usable channels.

If the AWS unit 4 determines that the number of unused channels is smaller than the maximum number N of usable channels, the processing transfers to step S38.

On the other hand, if the AWS unit 4 determines that the number of unused channels is not smaller than the maximum number N of usable channels, the processing advances to step S33. In this embodiment, under normal conditions, the AWS unit 4 secures a large value as a number of unused channels so that the endoscope 3 and endoscope system control apparatus 5 can be connected to each other at all times. Usually, therefore, the processing advances to step S33 based on a determination result of step S32.

In step S33, the AWS unit 4 performs processing for setting the minimum communication rate to the minimum effective rate×N. That is, the AWS unit 4 captures information on the effective communication rate at that point in time, and when the effective communication rate is varying, the AWS unit 4 sets as the minimum communication rate, the minimum effective communication rate, that is N times the minimum effective communication rate.

In a next step S34, the AWS unit 4 determines whether the minimum communication rate is not less than a required communication rate required by the side of the endoscope 3. If the AWS unit 4 determines that the minimum communication rate is less than the required communication rate, the processing advances to step S38.

On the other hand, if the AWS unit 4 determines that the minimum communication rate is not less than the required communication rate, the processing advances to step S35 based on the determination that communications are feasible.

In this manner, by performing wireless communications (connection) only when the required minimum communication rate (minimum communication speed) can be secured, it is possible to maintain a state where communications are performed even if communication conditions somewhat vary in the middle of a endoscope examination after its start.

In this step S35, considering the conditions of steps S33 and S34, the AWS unit 4 determines the number of initial usage channels. Thereafter, in a next step S36, the AWS unit 4 updates the number of unused channels and connection information.

Furthermore, in a next step S37, the AWS unit 4 performs processing for the establishment of activation message reception, thereby ending the activation message processing.

As described above, in this embodiment, when attempting to determine whether the target device is to be selected as a counterpart device for performing wireless transmission/reception of data, a determination is performed as to whether a predetermined communication rate can be secured, and only when the predetermined communication rate, namely, the minimum communication rate (minimum communication speed) can be secured besides ID information, the target device is selected as a counterpart device for performing wireless transmission/reception of data. This allows wireless transmission/reception to be stably performed.

In the above-described explanation with reference to FIG. 16A, the cases where the AWS unit 4 performs each of the steps were described, but the endoscope 3 may instead perform each thereof. For example, in step S4 in FIG. 14, the AWS unit 4 waits for reception of the activation message from the endoscope 3. Here, the AWS unit 4 may issue the activation message to the endoscope 3 and the endoscope 3 may perform processing of activation message reception to thereby perform processing in FIG. 16A during this reception.

In this case, (the CPU of) the state managing portion 81 of the endoscope 3 performs each of the steps in FIG. 16A. Furthermore, in this case, the state managing portion 81 of the endoscope 3 monitors a state where information including image data is wirelessly transmitted to the AWS unit 4, and has a function as determining means for determining whether a predetermined transmission speed is secured. The state managing portion 81 performs control for stopping the wireless transmission when the predetermined transmission speed is not secured.

According to this embodiment, therefore, in the endoscope system 1, when the endoscope 3, AWS unit 4, and endoscope system control apparatus 5, and the like are set to a state where wireless communication is performed, even if communication conditions somewhat vary, each of them can maintain a state where image data or fluid control data on air/water feed or the like are reliably transmitted/received.

In the above-described description, it was mentioned that the devices issuing the activation message include three pieces of information during the issuing of the activation message.

However, the activation message may include additional pieces of information as follows: (d) a maker ID (identification number of manufacturer in order that the determination of matched devices can be quickly made), and (e) an activation time (time when a transmission device for the activation message is activated; this is used for the determination of the order of priority).

In actuality, the AWS unit 4 performs the same processing also with respect to the endoscope system control apparatus 5. Also, the endoscope 3 performs the processing of activation message with the AWS unit 4, and performs the same processing with the endoscope system control apparatus 5.

Figure 16B:
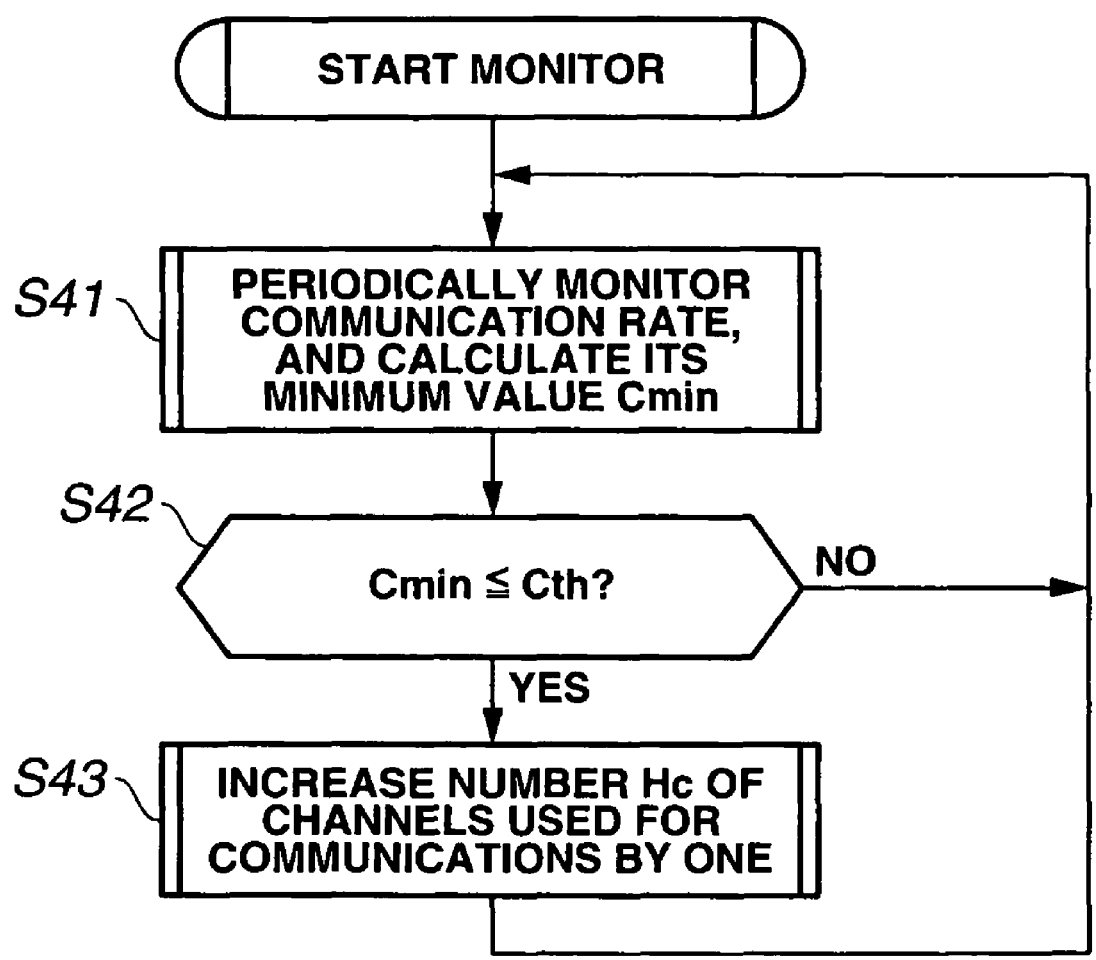
FIG. 16B is a flowchart showing contents of processing for changing the number of channels during communications.

The endoscope 3, AWS unit 4, or endoscope system control apparatus 5 may periodically monitor the effective communication rate, may secure the effective communication rate every time occasion demands, and may dynamically change the channel number into the channel number not less than the minimum value necessary the securing of the effective communication rate. FIG. 16B shows operations in this case.

FIG. 16B shows a state where e.g., the endoscope 3 and AWS unit 4 are performing communications under a channel number Hc. In step S41, the AWS unit 4 periodically calculates the minimum value Cmin per hour at a communication rate in all channels.

Then, as shown in step S42, the AWS unit 4 determines whether the minimum value Cmin of the calculated communication rate has reached a value of not more than a threshold value Cth that is set to a value a little larger than a required communication rate. If Cmin>Cth, the processing returns to step S41. On the other hand, if Cmin≦Cth, the processing advances to step S43, and after a channel number Hc used in communications has been increased by one, the processing returns to step S41.

Thereby, communications are started under a channel number set at an initial state, and even if a communication conditions deteriorates and the communication rate decreases, by increasing the cannel number used in communications, it is possible to secure a necessary communication rate and transmit information without interrupting communications.

In FIG. 16B, for the sake of simplicity, the case where the channel number is increased was described. However, when a sufficiently large effective communication rate can be provided, control for reducing channels may be performed. For example, when the current communication rate is large, estimation may be made as to whether a sufficient effective communication rate can be secured even if the channel number is reduced by one, and depending on this estimation result, control for reducing the channel number may be performed.

By these processings, the endoscope 3 starts image pickup operation by the CCD 25. Image pickup signals are wirelessly transmitted to the endoscope system control apparatus 5, and the endoscope image as shown in FIG. 13A is displayed on the observation monitor 6.

The UPD image by the AWS unit 4 is also wirelessly transmitted to the endoscope system control apparatus 5, and the UPD image as shown in FIG. 13A is displayed on the observation monitor 6.

Next, as a representative processing operation by the endoscope 3, operation contents of image pickup control processing will be described with reference to FIG. 17.

Figure 17:
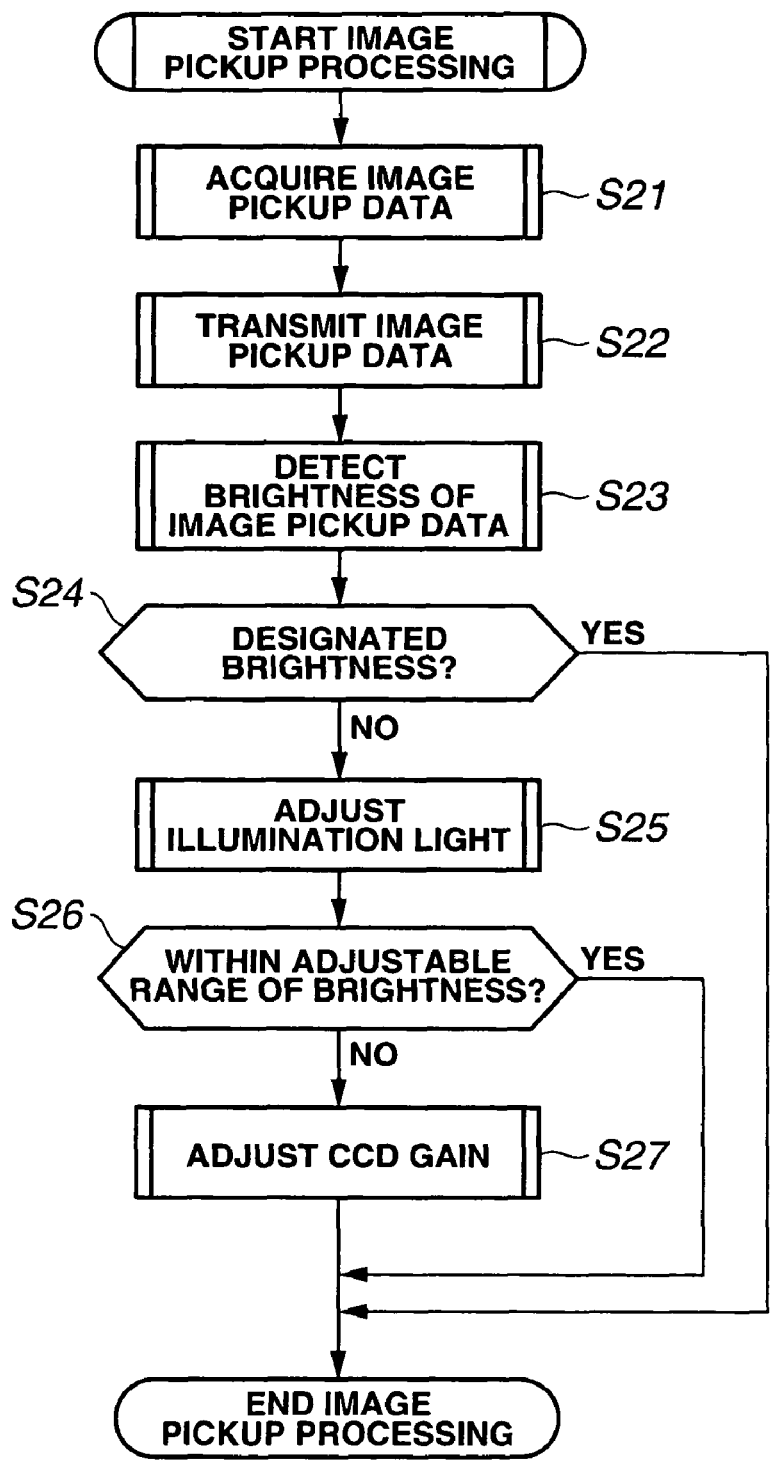
FIG. 17 is a flowchart showing operational contents of image-pickup control processing.

As shown in FIG. 17, upon the start of an image pickup processing, the endoscope 3 acquires image pickup data as shown in step S21. Specifically, under the management (control) of the state managing portion 81, the LED 56 emits light, as well as the CCD drive portion 86 starts an operation for driving the CCD 25, and image pickup signals picked up by the CCD 25 are converted into digital signals (image pickup data) by the ADC 87. The image pickup data (image data) is sequentially stored by the memory 88, and thereby an acquisition of the image pickup data is performed.

The acquired image data is sequentially transmitted as shown in step S22. The image data read from the memory 88 is wiredly transmitted from the transmission/reception unit 83 to the AWS unit 4, and wirelessly transmitted from the transmission/reception unit 77 of the AWS unit 4 to the endoscope system control apparatus 5. Then, the image data is converted into video signals inside the endoscope system control apparatus 5, and displayed on the observation monitor 6.

The image pickup data from the ADC 87 is inputted into the brightness detecting portion 89. As shown in step S23, the brightness detecting portion 89, for example, calculates an average value at an appropriate time, of luminance data on the image pickup data, and thereby performs a brightness detection.

The detection data of the brightness detecting portion 89 is inputted into, e.g., state managing portion 81, and a determination is made as to whether the brightness of image pickup data is a designated brightness (step S24). If the pertinent brightness is the designated one, the image pickup processing ends, and the processing transfers to a next image pickup processing.

On the other hand, in step S24, if the state managing portion 81 determines that the pertinent brightness is not the designated brightness, it sends an instruction signal (control signal) for illumination light adjustment to the illumination control portion 84. The illumination control portion 84 adjusts the amount of illumination light. For example, the illumination control portion 84 adjusts the illumination light by increasing or reducing the drive current for causing the LED 56 to emit light. The illumination control portion 84 returns this adjustment result to the state managing portion 81.

As a result, based on the information on the adjustment result, the state managing portion 81 determines by the illumination control portion 84 whether the pertinent brightness is within an adjustable range of brightness. If the brightness adjustment by the illumination control portion 84 suffices, this image pickup processing control ends without performing the processing in step S27. On the other hand, if the pertinent brightness is out of the adjustable brightness range by the illumination control portion 84, the state managing portion 81 outputs CCD gain adjustment signals to the CCD drive portion 86, and adjusts the CCD gain to thereby adjust the brightness of the image pickup data as shown in step S27. Thus, the image pickup processing ends.

According to the endoscope 3 of this embodiment, constituting the endoscope system 1, since signals for image data or fluid control data on air/water feed or the like can be transmitted/received by radio, an endoscope examination can be performed without the need to connect the endoscope 3 to each of endoscope peripheral apparatuses as transmission/reception counterparts by a cable.

Also, in this embodiment, the endoscope 3 has also air/water feed pipe line 60a and suction pipe line 61b, and hence, even if part of the visual field of the observation window is obstructed by adhesion of bodily fluids, the execution of air/water feed allows a predetermined visual field to be secured. In other words, according to this embodiment, it is also possible to ensure observation functionality. In contrast, in the conventional example, since a wireless type endoscope has no air/water feed pipe line 60a, it is difficult to sufficiently secure observation capability.

Furthermore, in this embodiment, during activation processing for starting an endoscope examination, determination processing is performed as to whether communications are possible at respective predetermined communication rates between endoscope peripheral apparatuses to be connected, and communications are performed by radio only when the communications can be performed at the respective predetermined communication rates. This can virtually eliminate the possibility that the transmission rate of image data significantly drop from a predetermined rate during an endoscope examination.

Moreover, according to this embodiment, by allowing the endoscope 3 to be separated into the endoscope body 18 and tube unit 19 in the operation portion 22, and making the tube unit 19 a disposable typed one, it is possible to easily perform the cleaning and sterilization of the endoscope body 18.

That is, as compared with the case of the conventional example, in which the tube unit 19 and a universal cable adaptable thereto are integrally formed, the air/water feed pipe line 60a and suction pipe line 61a in the endoscope body 18 can be made far short, thereby facilitating the cleaning and sterilization.

Also, in the case of the conventional example, in which the tube unit 19 and a universal cable adaptable thereto are integrally formed, the universal cable is contiguously arranged so as to be bended from the operation portion 22. On the other hand, in this embodiment, a little bent pipe line connector portion 51a is provided in the connector portion 51 of the operation portion 22 and the other portions are constituted of the air/water feed pipe line 60a and suction pipe line 61a that extend substantially linearly, so that processing such as the cleaning, sterilization, and drying etc. can be performed easily and in a short time. This makes it possible to set the endoscope 3 in a short time to a state that allows an endoscope examination to be performed.

Furthermore, in this embodiment, since the endoscope 3 is configured to detachably connect the endoscope body 18 and tube unit 19 in a contactless manner, no electrical contact is exposed on the external surface of the endoscope body 18. Hence, even if the endoscope body 18 is repeatedly cleaned and sterilized, there is no possibility of an occurrence of defective continuity, unlike the case where contactless connection is used. This leads to enhancement of reliability.

Also, in this embodiment, the operation portion 22 includes a large number of operating means, such as an angle operating means, air/water feed operation means, suction operating means, rigidity varying means, freeze operating means, release operating means. These operating means are intensively (concentratedly) controlled by the control circuit 57 provided in the operation portion 22. The control circuit 57 is configured to intensively control light emitting means for emitting illumination light for performing an image pickup and image pickup means for picking up an image together with the above-described operating means.

In this way, in this embodiment, various functions provided in the endoscope body 18 are intensively controlled by the control circuit 57 provided in the operation portion 22, as well as various functions for operating means for the AWS unit 4 connected to the endoscope body 18, and the endoscope system control apparatus 5 that performs transmission/reception of information by radio. Thereby, the user (more specifically, operator) can freely perform various operations by various operating means provided in the operation portion 22, resulting in significantly improved operability.

Particularly in this embodiment, by providing the control circuit 57 that performs intensive control, in the operation portion 22, image data obtained by image pickup by the CCD 25, and various signals from operating means can be efficiently transmitted from this control circuit 57.

Besides, since ones to be inserted into the tube unit 19 are reduced, the tube unit 19 can be decreased in diameter and can be made prone to bend, thereby improving an operability of the endoscope 3 when the user performs an operation.

Second Embodiment

Next, a second embodiment according to the present invention will be described with reference to FIGS. 18A to 18D. FIGS. 18A to 18C shows the configuration of an endoscope according to the second embodiment. Here, FIG. 18A is a partly cutaway side view of the neighborhood of the operation portion; FIG. 18B is a front view as seen from right side of FIG. 18A; FIG. 18C is a plan view as seen from above FIG. 18A; and FIG. 18D shows a portion of an endoscope 3F as a modification of the endoscope 3.

An endoscope 3B shown in FIGS. 18A to 18C, according to this embodiment has a hook 70 projectedly formed so as to surround both upper and lower ends of the holding portion 68 in the operation portion 22, in the endoscope 3 of the first embodiment, shown in FIG. 7. The hook 70 projects from both upper and lower ends of the holding portion 68, and these upper and lower halves are coupled together into a substantially U shape. Since the hook 70 is provided in this fashion, even in the event that the operator insufficiently holds the holding portion 68 and the endoscope 3 is trying to drop downward under to its weight, the hook 70 is constrained by an index finger or the like of the operator because the index finger or the like has been inserted inside the hook 70, and hence, the hook 70 performs the function of effectively preventing the dropping of the endoscope 3, namely, the function of assisting or enhancing the function of holding the holding portion 68.

In this embodiment, the antenna portion 141 provided inside the operation portion 22 is extended from the control circuit 57 provided inside the operation portion 22, and passed through the inside of the hook 70 so as to form a substantially L shape.

Also, in this embodiment, at an appropriate location on the way along the longitudinal direction of the insertion portion 21, there is provided a transparency sensor 143 for detecting the transparency of a fluid inside the air/water feed pipe line 60a and suction pipe line 61a. A detection signal from the transparency sensor 143 is sent to the control circuit 57.

Moreover, in this embodiment, a configuration is used such that the UPD coils 58 in the first embodiment are not provided. The other configurations are the same as those in the first embodiment.

According to this embodiment, by arranging the antenna portion 141 so as to pass through the inside of the hook 70, the antenna portion 141 can be formed longer than the case where the antenna portion 141 in the first embodiment is disposed in the vicinity of the upper end of the operation portion 22. This allows the function of receiving electric waves to be enhanced. In addition, the hook 70 is effectively utilized so as to improve the function of the antenna portion 141 besides the utilization of the original function of the hook 70 itself.

FIG. 18D shows the endoscope 3F as a modification. In the endoscope 3B shown in FIG. 18A and others, this endoscope 3F has not the lower end portion of the hook 70 formed in the substantially U shape, but has a substantially L shape hook 70'. That is, the endoscope 3F has the hook 70' formed into the substantially L shape from the upper end portion in the holding portion 68 provided on the rear end (upper end) side of the holding portion 68.

This modification also has the antenna portion 141 inside the hook 70'.

This modification has substantially the same effect as that of the endoscope 3B in FIG. 18A.

Third Embodiment

Figure 19:
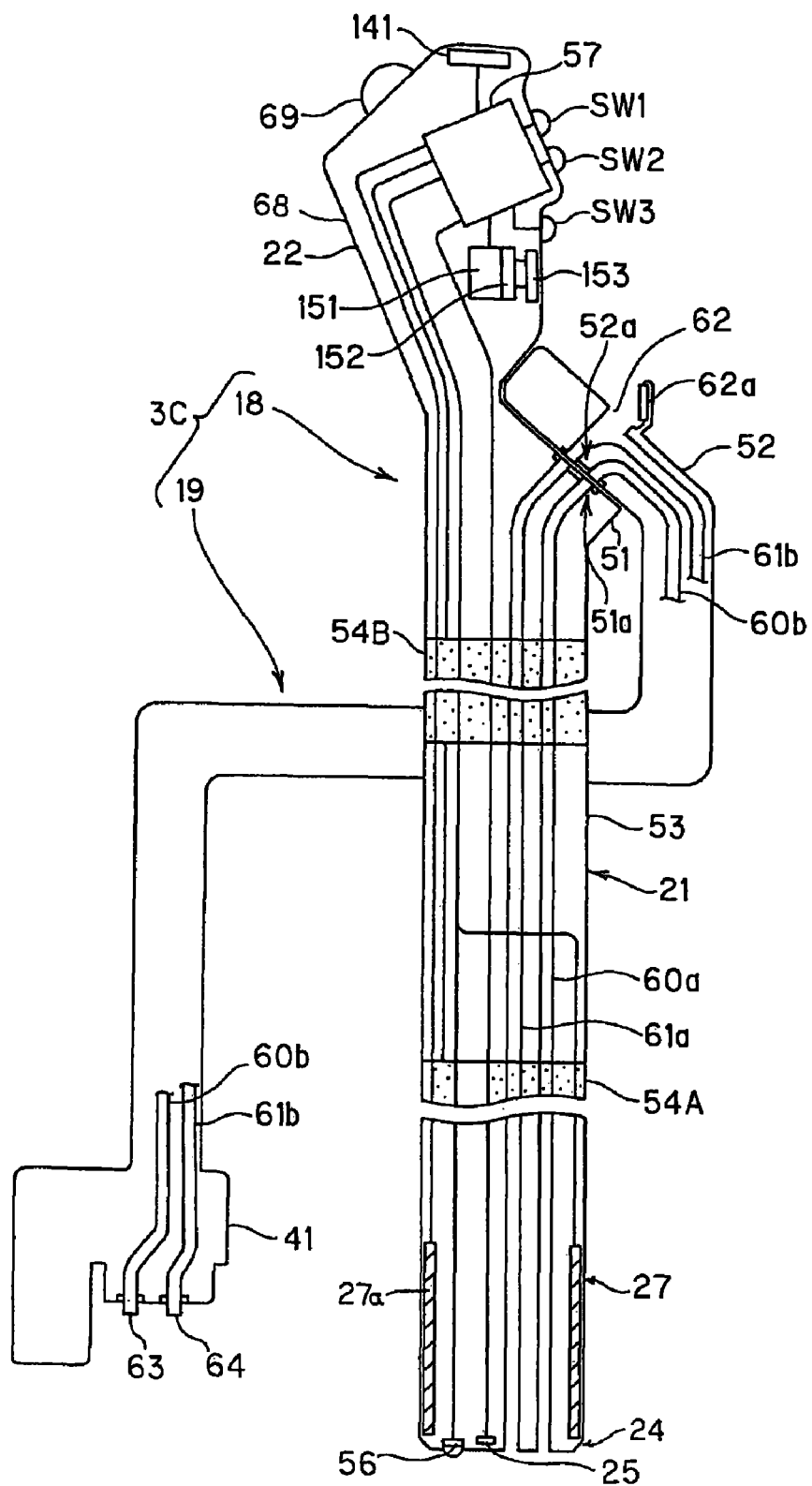
FIG. 19 is diagrams each showing an endoscope according to a third embodiment of the present invention.

A third embodiment according to the present invention will be described with reference to FIG. 19. FIG. 19 shows the configuration of an endoscope 3C according to the third embodiment.

As shown in FIG. 19, the endoscope 3C according to this embodiment has the antenna portion 141 in the operation portion 22 as in the case of the endoscope 3 in FIG. 7, and performs the transmission/reception of signal data by the antenna portion 141. Furthermore, in the operation portion 22, the endoscope 3C has a battery 151, and a charging circuit 152 and a noncontact charging coil 153 that are connected to the battery 151, without having the power supply line 71a.

Therefore, the connector portion 51 of the operation portion 22 in this embodiment constituted of only the pipe line connector portion 51a comprising an air/water feed connector and suction connector.

As a result, the tube unit 19 that is detachably connected to the endoscope body 18 has no power supply line 73a, and has only the pipe line tubes of the air/water feed pipe line 60b and suction pipe line 61b that are arranged through the tube unit 19. That is, in this embodiment, the tube unit 19 substantially consists of a tube unit (cable unit) through which a pipe line system alone is arranged.

The above-described battery 151 is constituted of a secondary battery capable of charging a lithium battery and the like, and is connected to the watertight structured noncontact charging coil 153 that is incorporated at a part near the external surface of the operation portion 22, via the charging circuit 152. Opposing a noncontact power-feeding coil (not shown) to the external surface of the part in which the noncontact charging coil 153 is incorporated, and supplying an AC current to this noncontact power-feeding coil, allows the battery 151 to be charged.

In other words, by supplying AC power to the noncontact charging coil 153 arranged on the external surface side of the operation portion 22, it is possible to transmit the AC power to the noncontact charging coil 153 inside the operation portion 22 in a noncontact manner by electromagnetic coupling. This AC power is converted into DC voltage for charging the battery 151 by the charging circuit 152, and supplied to the battery 151, thereby charging the battery 151.

In this embodiment, as described also in the first embodiment, since the LED 56 is adopted as illumination means, power consumption can be far reduced compared with the case where a lamp is used, and a ultrasensitive CCD 25 (incorporating a variable gain function) as an image pickup element, a sufficiently bright image can be achieved even in a state where the illumination light amount is small. As a result, even when the battery 151 is adopted, an endoscope examination can be performed for a far long time compared with the case of the conventional example. Also, as the battery 151, compact and lightweight one as compared with the conventional example can be adopted, so that a satisfactory operability can be ensured by reducing the weight of the operation portion 22.

According to this embodiment, the tube unit 19 is constituted of a pipe line system alone, which makes the tube unit 19 more prone to suit the disposable type. Even when the tube unit 19 is recycled (reused), the absence of wire in the tube unit 19 facilitates the recycling.

Also, according to this embodiment, when the pipe line system is not used, the endoscope 3 can be used with the tube unit 19 detached from the endoscope body 18. That is, in this case, since the tube unit 19 can be dispensed with, it is possible to eliminate the tube unit 19 getting in the way of operations, resulting in improved operability.

Other operations and effects are substantially the same as those in the cases described in the first and second embodiments.

Next, description is made of another endoscope system with reference to FIGS. 20A to 20C and FIG. 21. This endoscope system has a configuration wherein, for example, in the endoscope system 1 of the first embodiment, the operator who holds the endoscope 3 can operates various operations by operating the trackball 69 and/or the like provided in the vicinity of holding portion 68, and further there is provided an operation remote controller 207 so that other operators who conduct together an operative treatment or the like can also perform operations such as air/water feed and/or suction.

The operation remote controller 207 is supplied with power from e.g., the AWS unit 4 via a connection cable 208 that is detachably connected to the bottom of the operation remote controller 207.

The operation remote controller 207 has, for example, the same external shape as that of the holding portion 68 in the endoscope 3B in FIGS. 18A, 18B and 18C. That is, a holding portion 217 has switches SW1 to SW3 on the center line C of the holding portion 217 along the longitudinal direction, and has a substantially U shape hook 218 formed so as to cover both ends of the switches SW1 to SW3.

The upper end face of the holding portion 217 constitutes a slope Sa. A trackball 219 is arranged at a location on the slope Sa, opposite to the e switches SW1 to SW3, and the switches SW4 and SW5 are arranged on both sides of the trackball 219. By operations of the trackball 219, and the switches SW1 to SW 5, the same operations as those on the side of the endoscope 3 can be performed.

A control circuit 257 is accommodated inside the operation remote controller 207. The control circuit 257 is connected to an antenna portion 215 constituting a transmission unit 283 (refer to FIG. 21). The antenna portion 215 is disposed in the hook 218.

A power supply coil 208a provided at one end of the connection cable 208 is detachably connected to a power-transmission receiving portion 210 provided at the bottom of the operation remote controller 207. An AC power supply is adapted to be able to be supplied to the power-transmission receiving portion 210 from the AWS unit 4 to which the other end of the connection cable 208 is connected.

FIG. 21 shows the configuration of an electrical system of the operation remote controller 207.

The control circuit 257 inside the operation remote controller 207 has therein a state managing portion 281 constituted of the CPU etc. managing controlled state of each portion. The state managing portion 281 is connected to a state holding memory 282 that holds (stores) a state of each portion, and also connected to a transmission/reception unit 283 of wireless type. The transmission/reception unit 283 performs transmission/reception between the transmission/reception unit 83 of the endoscope 3 and transmission/reception unit 77 of the AWS unit 4.

The state managing portion 281 is connected to a trackball displacement detecting portion 284 for detecting a displacement amount of the trackball 219 that is disposed at a location allowing the user to operate the trackball by the operator's hand holding the holding portion 217, on an external surface (including the slope Sa) of the operation remote controller 207. The state managing portion 281 holds the detected displacement amount in a state holding memory 282, as well as sends it to the data communication control portion 11 of the transmission/reception unit 283 and transmits it to the endoscope 3.

Furthermore, the air/water feed switch SW4, suction switch SW5, and function switches SW1 to SW3 are connected to a switch push detecting portion 285 that is disposed at a location allowing the user to operate the switches by the operator's hand holding the holding portion 217, on the external surface of the operation remote controller 207. The switch push detecting portion 285 detects an ON/OFF state when each of the switches is pushed. The detected signal is outputted to the state managing portion 281.

The state managing portion 281 holds the detected state of each of the switches in the state holding memory 282, as well as sends it to the data communication control portion 11 of the transmission/reception unit 283 and transmits it to the endoscope 3. A power generating portion 286 provided inside the control circuit 257 is connected to the power-transmission receiving portion 210, and after having converted AC power transmitted from the AWS unit 4 into DC power, supplies power for operations to each portion inside the control circuit 257.

According to the present system, operators other than the operator who holds the endoscope 3 can also perform the bending operation (angle operation) and/or fluid control operation. This allows an operational treatment or the like performed by a plurality of operators to be more smoothly carried out.

Meanwhile, embodiments and the like formed by partly combining the above-described embodiments are also subsumed under the present invention. Furthermore, modifications formed by modifying some of the embodiments are also subsumed under the present invention. For example, arrangements modified by shifting the connection portion of the tube unit 19 from the holding portion 68 or operation portion 22 to the base end (rear end) side of the insertion portion 21 are also basically subsumed under the present invention.

What is claimed is:

1. An endoscope comprising:
   an elongated insertion portion,
   an operation portion provided at the rear end of the insertion portion;
   an image pickup portion provided at the front end of the insertion portion, for picking up an image of a subject;
   an antenna provided in the operation portion;
   a wireless transmission portion for wirelessly transmitting, using the antenna, information including image data on the subject obtained by the image pickup portion, to endoscope peripheral apparatuses in the outside; and
   a determining portion for determining whether a predetermined transmission speed can be secured when information is wirelessly transmitted by the wireless transmission portion, and for prohibiting the transmission of information by the wireless transmission portion when it has been determined that the predetermined speed cannot be secured.

2. The endoscope according to claim 1,
   wherein the operation portion comprises a holding portion for an operator to operate, the holding portion being disposed at the periphery of the rear end of the operation portion; and
   wherein the antenna is disposed in a projection portion projected from the rear end of the holding portion in order to increase the holding capability of the holding portion.

3. The endoscope according to claim 1, wherein the endoscope is configured to be of a contactless structure in which no electrical contact is exposed to the external surface of the endoscope.

4. The endoscope according to claim 1, further comprising:
   a connection portion of a contactless structure, the connection portion being disposed at the periphery of the operation portion,
   wherein a tube unit having the contactless structure at one end thereof, is detachably connected to the connection portion.

5. The endoscope according to claim 4, wherein the elongated insertion portion has therein an air/water feed pipe line, and an air/water feed tube that is detachably connected to the air/water feed pipe line is arranged through the tube unit.

6. The endoscope according to claim 4, further comprising:
   an air/water feed pipe line provided in the elongated insertion portion, and
   a suction pipe line serving as a passage for sucked fluids,
   wherein an air/water feed tube and a suction tube that are detachably connected to the air/water feed pipe line and the suction pipe line, respectively, are arranged through the tube unit.

7. The endoscope according to claim 4, wherein a power supply line for supplying power to the image pickup portion in the operation portion, is arranged through the tube unit.

8. The endoscope according to claim 7, further comprising:
   a DC power generating portion for generating DC power from AC power supplied to the periphery of the operation portion via the power supply line.

9. The endoscope according to claim 7, wherein the DC power generating portion comprises:
   a DC power supply circuit for radio, the DC power supply circuit for radio supplying DC power to the wireless transmission portion; and
   a DC power supply circuit for drive, the DC power supply circuit for drive supplying DC power to a drive portion for driving the image pickup portion and the like.

10. The endoscope according to claim 1, further comprising:
    a battery for supplying DC power to the image pickup portion, the wireless transmission portion, and the like, the battery being disposed at the periphery of the operation portion including the operation portion.

11. The endoscope according to claim 10, wherein the battery is a chargeable secondary battery.

12. The endoscope according to claim 1,
    wherein the insertion portion comprises a freely bendable bending portion; and wherein, at the periphery of the operation portion including the operation portion, there is provided an instruction operation portion having, in combination, a function of performing a bending instruction operation with respect to the bending portion, and a function of performing an instruction operation other than the bending instruction operation.

13. The endoscope according to claim 1, wherein, in the insertion portion, a plurality of shape detection devices for detecting the shape of the insertion portion are arranged along the longitudinal direction of the operation portion.

14. An endoscope comprising:
an elongated insertion portion having therein an air/water feed pipe line;
an operation portion provided at the rear end of the insertion portion;
an image pickup portion provided at the front end of the insertion portion, for picking up an image of a subject;
an antenna provided in the operation portion;
a wireless transmission portion for wirelessly transmitting, using the antenna, information including image data on the subject obtained by the image pickup portion, to endoscope peripheral apparatuses in the outside; and
a connection portion of a contactless structure, the connection portion being disposed at the periphery of the operation portion, wherein
a tube unit having the contactless structure at one end thereof, is detachably connected to the connection portion,
an air/water feed tube that is detachably connected to the air/water feed pipe line is arranged through the tube unit, and
a power supply line for supplying power to the image pickup portion in the operation portion, is arranged through the tube unit.

15. An endoscope comprising:
an elongated insertion portion having therein an air/water feed pipe line;
an operation portion provided at the rear end of the insertion portion;
an image pickup portion provided at the front end of the insertion portion, for picking up an image of a subject;
an antenna provided in the operation portion;
a wireless transmission portion for wirelessly transmitting, using the antenna, information including image data on the subject obtained by the image pickup portion, to endoscope peripheral apparatuses in the outside;
a connection portion of a contactless structure, the connection portion being disposed at the periphery of the operation portion; and
a suction pipe line serving as a passage for sucked fluids, wherein
a tube unit having the contactless structure at one end thereof, is detachably connected to the connection portion,
an air/water feed tube and a suction tube that are detachably connected to the air/water feed pipe line and the suction pipe line, respectively, are arranged through the tube unit, and
a power supply line for supplying power to the image pickup portion in the operation portion, is arranged through the tube unit.

* * * * *